(12) United States Patent
Grote et al.

(10) Patent No.: US 7,985,858 B2
(45) Date of Patent: Jul. 26, 2011

(54) PROCESS FOR THE PREPARATION OF 6-ALPHA-HYDROXY-N-ALKYLATED OPIATES

(75) Inventors: Christopher W. Grote, Webster Groves, MO (US); Peter X. Wang, Chesterfield, MO (US); Tao Jiang, St. Louis, MO (US); Gary L. Cantrell, Troy, IL (US); Frank W. Moser, Arnold, MO (US); Catherine E. Thomasson, Webster Groves, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 372 days.

(21) Appl. No.: 12/444,421

(22) PCT Filed: May 2, 2008

(86) PCT No.: PCT/US2008/062413
§ 371 (c)(1),
(2), (4) Date: Apr. 6, 2009

(87) PCT Pub. No.: WO2008/137672
PCT Pub. Date: Nov. 13, 2008

(65) Prior Publication Data
US 2010/0041888 A1    Feb. 18, 2010

Related U.S. Application Data

(60) Provisional application No. 60/915,962, filed on May 4, 2007, provisional application No. 60/949,055, filed on Jul. 11, 2007.

(51) Int. Cl.
*C07D 489/08* (2006.01)
*C07D 489/02* (2006.01)
(52) U.S. Cl. ......................................... 546/46; 546/45
(58) Field of Classification Search .................... 546/46, 546/45
See application file for complete search history.

(56) References Cited

U.S. PATENT DOCUMENTS

| | | | |
|---|---|---|---|
| 2,772,270 | A | 11/1956 | Weiss |
| 4,089,855 | A | 5/1978 | Chatterjie et al. |
| 4,443,605 | A | 4/1984 | Kotick et al. |
| 4,673,679 | A | 6/1987 | Aungst et al. |
| 4,775,759 | A | 10/1988 | Rice et al. |
| 4,795,813 | A | 1/1989 | Schwartz |
| 4,912,114 | A | 3/1990 | Revesz |
| 5,240,933 | A | 8/1993 | Merz et al. |
| 5,336,483 | A | 8/1994 | de Costa et al. |
| 5,668,285 | A | 9/1997 | Rice et al. |
| 5,693,820 | A | 12/1997 | Helmchen et al. |
| 5,756,745 | A | 5/1998 | Kavka |
| 6,184,381 | B1 | 2/2001 | Ikariya et al. |
| 6,509,467 | B1 | 1/2003 | Blacker et al. |
| 7,045,646 | B2 | 5/2006 | Tanis et al. |
| 2006/0182692 | A1 | 8/2006 | Fishburn et al. |

FOREIGN PATENT DOCUMENTS

| | | |
|---|---|---|
| EP | 0 034 480 | 8/1981 |
| EP | 0 879 823 | 11/1998 |
| WO | WO 95/32973 | 12/1995 |
| WO | WO 98/05667 | 2/1998 |
| WO | WO 2005/100361 | 10/2005 |
| WO | WO 2006/008562 | 1/2006 |
| WO | WO 2006/035195 | 4/2006 |
| WO | WO 2006/052710 | 5/2006 |

OTHER PUBLICATIONS

Van Gurp et al., "Synthesis of 7,8-Didehydro-3,4-Dimethoxy . . . ", Bull. Soc. Chim. Belg., vol. 96/n° Apr. 1987, p. 325-329.
Uwai et al., "Syntheses and receptor-binding studies of derivatives . . . ", Bioorganic & Medicinal Chemistry, 12, 2004, p. 417-421, XP 002488979.
Malspeis et al., "Metabolic Reduction of Naltrexone I. Synthesis, Separation . . . ", Res. Commun. Chem. Pathol. Pharmacol, 2(43), 1975.
Olsen et al., "Conjugate Addition Ligands of Opioid Antagonists . . . ", J. Med. Chem., 1990, 33(2), p. 737-741.
Koolpe et al., "Opioid Agonists and Antagonists. 6-Desoxy-6-substituted . . . ", J. Med. Chem., 1985, 28(7), p. 949-957.
Fuiji et al., "Ruthenium(II)-Caatalyzed Asymmetric Transfer . . . ", J. Am. Chem. Soc., 1996, 118, p. 2521-2522.
Yamakawa et al., "The Methal-Ligand Bifunctional Catalysis: A Theoretical Study on . . . ", J. Am. Chem. Soc., 2000, 122, p. 1466-1478.
Uematsu et al., "Asymmetric Transfer Hydrogenation of Imines", J. Am. Chem. Soc., 1996, 118, p. 4916-4917.
Wu et al., "Asymmetric transfer hydrogenation of imines and iminiums . . . ", Chem. Commun., 2006, p. 1766-1768.
Mao et al., "A Chiral Rhodium Complex for Rapid Asymmetric Transfer . . . ", Organic Letters, 1999, vol. 1, No. 6, p. 841-843.
Uba et al., "Stereospecific Synthesis of Codeine . . . ", Chem. Pharm. Bull., vol. 27, Issue 9, 1979, p. 2257-2258.
Leland et al., "Analgesic narcotic antagonists. 5. 7,7-Dimethyldihydrocodeinones . . . ", J. Med. Chem.., 1981, 24, p. 717-721.
Burke et al., "Probes for narcotic Receptor Mediated Phenomena . . . ", Heterocycles, vol. 23, No. 1, 1985, p. 99-110.
Sagara et al., "Specific Affinity Labeling of . . . ", Bioorganic & Medicinal Chemistry Letters, vol. 5, No. 15, 1995, p. 1609-1614.
Gao et al., "Synthesis of 7-Arylmorphinans . . . ", J. Med. Chem., 1998, 41, p. 3901-3098.
White et al., "Asymmetric Total Synthesis of (+)-Codeine via . . . ", J. Org. Chem., 1999, 64, p. 7871-7884. Fuiji et al., "The First Example of the Stereoselective Synthesis of . . . ", Chem. Pharm. Bull., 52(6), 2004, p. 747-750.

(Continued)

*Primary Examiner* — Charanjit Aulakh

(57) ABSTRACT

The present invention is directed to the conversion of a 6-keto morphinan to a 6-alpha-hydroxy morphinan in the presence of a ruthenium, rhodium, or iridium asymmetric catalyst and a hydrogen source.

21 Claims, No Drawings

OTHER PUBLICATIONS

Kalimin et al., "Palladium-Catalyzed 2-Phenylethenylation of Codeine . . . ", Helevetica Chimca Acta, vol. 89, 2006, p. 861-869.

Chatterjie et al., "Reduction of 6-Ketones of the Morphine Series . . . ", J. Org. Chem., vol. 41, No. 22, 1976, p. 3624-3625.

Brine et al., "Formamidinesulfinic Acid Reduction of Dihydrocodeinone Derivatives", J. Org. Chem., vol. 43, No. 8, 1978, p. 15551557.

De Costa et al., "Probes for Narcotic Receptor Mediated Phenomena . . . ", J. Med. Chem., 19972, 35, p. 2826-2835.

Olieman et al., "Conversion of (−)-dihydrocodeinone into . . . ", Laboratory of Organic chemistry Technische Hogeschool Delft, Julianalaan 136, Delft, The Netherlands, Mar. 15, 1976.

White et al., "Asymmetric Synthesis of (+)-Morphine . . . ", J. Org. Chem., 1997, 62, p. 5250-5251.

Borch et al., "The cyanohydridoborate Anion as a Selective Reducing Agent", Journal of the American Chemical Society, 93:12, Jun. 16, 1971, p. 2897-2904.

Abdel-Magid et al., "Reductive Animation of Aldehydes and Ketones . . . ", Tetrahedron Letters, vol. 31, No. 39, 1990, p. 5395-5598.

Gribble et al., "Reactions of Sodium Borohydride in Acidic Media . . . ", Communications, Aug. 1987, p. 709-711.

Campbell et al., "The Preparation of Unsymmetrical Secondary Aliphatic Amines", Jan. 1944, vol. 66, p. 82-84.

Hashiguchi et al., "Asymmetric Transfer Hydrogenation of Aromatic ketones Catalyzed by chiral Ruthenium(II) Complexes", J. Am. Chem. Soc., vol. 177, No. 28, 1995, p. 7562-7563.

Palmer et al., "Asymmetric transfer hydrogenation of C=O and C=N bonds", Tetrahedron: Asymmetry 10, 1999, p. 2045-2061, XP 004174087.

Schellenberg, "The Synthesis of Secondary and Tertiary Amines by Borohydride Reduction", Nov. 1963, p. 3259-3261.

Spadoni et al., "2-[N-Acylamino($C_1$—$C_3$)alkyl]indoles as $MT_1$ . . . ", J. Med. Chem., 1998, 41, p. 3624-3634.

Ohno et al., "Solid-Phase synthesis of 6-Sulfionylamino Morphinan Libraries", Synlett, 2002, No. 1, p. 93-96.

Lazar et al., "A Selective Removal of Benzyl Protecting Groups in Arylphosphate Esters with Bromotrimethylsilane", Synthetic Communications, 22(6), 1992, p. 923-931.

Butora et al., "Chemoenzymatic Synthesis of the Morphine Skeleton via Radical . . . ", Tetrahedron Letters, vol. 37, No. 45, 1996, p. 8155-8158.

Watanabe et al., "Novel Synthesis of the Ortho Ester Derivative of 4,5-Epoxymorphinan", Organic Letters, vol. 8, No. 3, 2006, p. 523-526.

Nagase et al., "The Facility of Formation of a $\Delta^6$ Bond in Dihydromorphinone and Related Opiates", J. Org. Chem., 1989, 54, p. 4120-4125.

"A New Reagent for the Selective, High-Yield N-Dealkylation of Teritary Amines: Improved Syntheses of Naltrexone and Nalbuphine", J. Org. Chem.., 1984, 49, p. 2081-2082.

Gorlitzer et al., "Diepoxy-bis-(iminoethano)-dinaphth[2,1-b:1′,2′-i]acridine $^{2,3+}$)", Arch. Pharm. (Weinheim) 325, 1992, p. 637-641.

Lau et al., "Evolutiion of a Series of Non-Quinoline Leukotriene $D_4$ Receptor Antagonist . . . ", Bioorganic & Medicinal chemistry Letters, vol. 5, No. 15, 1995, p. 1615-1620.

Schmidhammer, "134. Synthesis and Biological ion of 14-Alkoxymorphinans Part 4) Opioid Agonists and Partial Opioid Agonists in a Series of . . . ", Helevitca Chimca Acta, vol. 72, 1989, p. 1233-1239.

Bognar et al., Izvestiya po Khimiya, 1975, 81(1), p. 203-215.

Noyori et al., "Asymmetric Catalysts by Architechtural and Functional Molecular . . . ", Agew. Chem.. Int., Ed. 2001, 40, p. 40-73.

Borch et al., "A New Method for the Methylation of Amines", J. Org. Chem., vol. 36, No. 10, 1972, pp. 1673-1674.

Olofson et al., "A New Reagent for the Selective, High-Yield N-Dealkylation of Tertiary Amines: Improved Syntheses of Naltrexone and Nalbuphine", Journal of Organic Chemistry, 49, 1984, pp. 2081-2082, XP 000615842.

Iijima et al., "Studies in the (+)-Morphinan Series. 5. Synthesis and Biological Properties of (+)-Naloxone", Journal of Medicinal chemistry, 1978, 21(4), pp. 398-400, XP 002428747.

Gates et al., "Some Potent Morphine Antagonists Possessing High Analgesic Activity", Journal of Medicinal Chemistry, 7(2), 1964, pp. 127-131, XP 009097368.

March, "Advanced Organic Chemistry", 1985, pp. 800-802, XP 002571909.

Ullrich et al., "Derivatives of 17-(2-Methylallyl)-substituted Noroxymorphone: Variation of the Delta Address and Its Effects on Affinity and Selectivity for the Delta Opiod Receptor", Biooorganic & Medicinal Chemistry Letters, 11(21), 2001, pp. 2883-2885, XP 002561406.

Jacobson et al., "Paradoxical Effects of N-Cyanoalkyl Substituents upon the Activities of Several Classes of Opioids", Journal of Medicinal Chemistry, 1979, 22(3), pp. 328-331, XP 002252852.

Database Beilstein, Beilstein Institute for Organic Chemistry, 2000, XP 002571908.

PROCESS FOR THE PREPARATION OF 6-ALPHA-HYDROXY-N-ALKYLATED OPIATES

CROSS REFERENCE TO RELATED APPLICATIONS

This application is a national stage application of PCT/US2008/062413, filed May 2, 2008, which claims the benefit of U.S. Provisional Application No. 60/915,962 filed May 4, 2007 and U.S. Provisional Application No. 60/949,055 filed Jul. 11, 2007.

FIELD OF THE INVENTION

The present invention generally relates to processes for the synthesis of intermediate or end product morphinans. More specifically, the invention is directed to the synthesis of 6-alpha-hydroxy morphinans and salts, intermediates, and analogs thereof.

BACKGROUND OF THE INVENTION

The reduction of the 6-keto group of certain morphinans is a necessary step in the preparation of many opiate-based compounds such as nalbuphine. Traditionally, the 6-keto group has been reduced using boron reducing agents, e.g., $NaBH_4$, at reduced temperatures. See, for example, R. Van Gurp et al., *Chemistry of Opium Alkaloids. Part XXIV. Synthesis of 7,8-didehydro-3,4-dimethoxy-17-methylmorphinan-6-one and the Regioselective Reduction of the Keto Function*, Neth. Bulletin des Societes Chimiques Belges 96(4), pp. 325-9 (1987) and K. Uwai et al., *Syntheses and Receptor-binding Studies of Derivatives of the Opioid Antagonist Naltrexone*, Bioorg. & Med. Chem., 12, p. 417 (2004). For this synthetic route, the reduced temperatures provide the desired excess of the 6-α-hydroxy epimer. Depending on the temperature, the epimeric ratio can be as high as 99:1 6α:6β hydroxy at temperatures below −20° C. Higher temperatures tend to erode this ratio resulting in an increased percentage of the 6-β-hydroxy epimer. Other boron-derived reducing agents have improved on this ratio and have allowed the reaction to be conducted at more reasonable temperatures. See, for example, L. Malspeis et al., *Metabolic Reduction of Naltrexone. I. Synthesis, Separation, and Characterization of Naloxone and Naltrexone Reduction Products and Qualitative Assay of Urine and Bile Following Administration of Naltrexone, α-Naltrexol, or β-Naltrexol*, Res. Commun, Chem. Pathol. Pharmacol. 2(43) (1975); L. Olsen at al., *Conjugate Addition Ligands of Opioid antagonists. Methacrylate Esters and Ethers of 6α-and 6β-naltrexol*, J. Med. Chem., 33(2), pp. 737-41 (1990); and G. Koolpe at al., *Opioid Agonists and Antagonists. 6-Desoxy-6-substituted Lactone, Epoxide, and Glycidate Ester Derivatives of Naltrexone and Oxymorphone*, J. Med. Chem., 28(7), pp. 949-57 (1985).

Upon completion of the reaction and destruction of any excess reducing reagent, the reduced opiate is typically isolated by extraction. The isolation methods, however, typically fail to supply useful quantities of the desired compounds. Instead, the yields tend to be low and purification difficult. Repeated extractions using chloroform are normally necessary to liberate the product from the reaction. After the extraction process is complete, a lengthy distillation is necessary to remove the excess chloroform. The yields for the conversion process utilizing the boron reducing groups varies widely, from about 50 to 90%. In addition, under certain conditions, crystallization of the product is essential to raise the epimeric purity.

Accordingly, a need exists for a convenient and efficient method of converting 6-keto morphinans to 6-α-hydroxy morphinans. This method should ensure high epimeric purity and also allow for simplified isolation of the desired compound.

SUMMARY OF THE INVENTION

Among the various aspects of the present invention is the provision of a process for the conversion of a 6-keto morphinan to a 6-α-hydroxy morphinan in the presence of a ruthenium, rhodium, or iridium asymmetric catalyst and a hydrogen source. The 6-α-hydroxy morphinan may further be derivatized, if desired, in one or more additional steps to form a 6-α-hydroxy-N-alkylated morphinan compound. Alternatively, in certain circumstances, N-alkylation may be performed in tandem with the conversion of the 6-keto morphinan to the 6-α-hydroxy morphinan. In another aspect of the present invention, N-alkylation of the morphinan, if desired, is preformed prior to the conversion of the 6-keto to the 6-α-hydroxy morphinan.

Briefly, therefore, the present invention is directed to a process for the preparation of a 6-α-hydroxy morphinan having the formula (II),

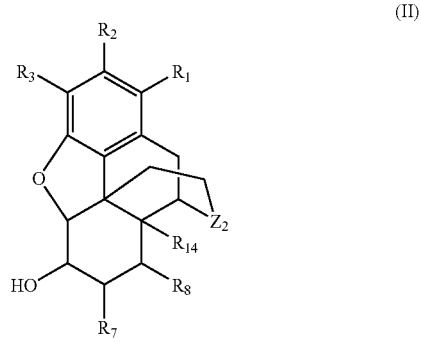

(II)

the process comprising reducing a 6-keto morphinan (1) in the presence of a ruthenium, rhodium, or iridium asymmetric catalyst and a hydrogen source, the 6-keto morphinan (1) having the formula:

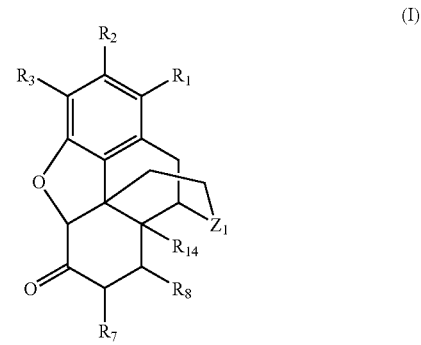

(I)

wherein
$R_1$ is hydrogen, hydrocarbyl, substituted hydrocarbyl, halo, or $—OR_{111}$;

$R_2$ is hydrogen, hydrocarbyl, substituted hydrocarbyl, halo, or —$OR_{211}$;

$R_3$ is hydrogen, hydrocarbyl, substituted hydrocarbyl, or —$OR_{311}$;

$R_7$ is hydrogen, hydrocarbyl, substituted hydrocarbyl, or —$OR_{711}$;

$R_8$ is hydrogen, hydrocarbyl, substituted hydrocarbyl, or —$OR_{811}$;

$R_{14}$ is hydrogen or hydroxy;

$R_{111}$ is hydrogen, hydrocarbyl, substituted hydrocarbyl, or a hydroxy protecting group;

$R_{211}$ is hydrogen, hydrocarbyl, substituted hydrocarbyl, or a hydroxy protecting group;

$R_{311}$ is hydrogen, hydrocarbyl, substituted hydrocarbyl, or a hydroxy protecting group;

$R_{711}$ is hydrogen, hydrocarbyl, substituted hydrocarbyl, or a hydroxy protecting group;

$R_{811}$ is hydrogen, hydrocarbyl, substituted hydrocarbyl, or a hydroxy protecting group;

$Z_1$ is >$N(R_9)$, >$N^+(R_9)(R_{10})$, >$NCH(OH)(R_9)$, or >$N^+$=$CH(R_9)$;

$Z_2$ is
(i) $Z_1$ when $Z_1$ is >$N(R_9)$ or >$N^+(R_9)(R_{10})$; or
(ii) >$NCH_2(R_9)$ when $Z_1$ is >$NCH(OH)R_9$ or >$N^+$=$CH(R_9)$; and $R_9$ and $R_{10}$ are independently hydrogen, acyl, hydrocarbyl, substituted hydrocarbyl, or heterocyclo.

Other objects and features will be in part apparent and in part pointed out hereinafter.

DETAILED DESCRIPTION OF THE INVENTION

The present invention is directed to improved synthetic methods for the preparation of 6-α-hydroxy morphinans, salts, intermediates, and analogs thereof. In one aspect of the present invention, the synthetic methods utilize a ruthenium, rhodium, or iridium asymmetric catalyst and hydrogen source to selectively convert 6-keto morphinans to 6-α-hydroxy morphinans. Advantageously, a wide range of reaction conditions can be used to effect this reaction.

Using the process described herein, the conversion of the 6-keto to the 6-hydroxy group results in a mixture 6-α-hydroxy and 6-β-hydroxy morphinan epimers. Typically, the epimeric ratio of 6-α-hydroxy to 6-β-hydroxy morphinan epimers is greater than 9:1 and often greater than 19:1. In one example, the epimeric ratio of 6-α-hydroxy to 6-β-hydroxy morphinan epimers is greater than 99:1, preferably greater than 99.5:1.

Morphinan Compounds

For purposes of discussion, the ring atoms of the morphinans of the present invention are numbered as follows:

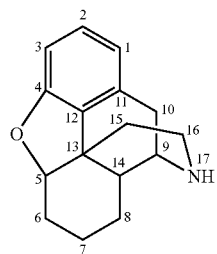

As illustrated in the core morphinan structure, there may be four chiral carbons, i.e., C-5, C-13, C-14, and C-9.

Further, for purposes of illustration, the $Z_1$ moieties of the morphinans of the present invention, >$N(R_9)$, >$N^+(R_9)(R_{10})$, >$NCH(OH)(R_9)$, and >$N^+$=$CH(R_9)$, correspond to Formulae (Ia), (Ib), (Ic) and (Id), respectively:

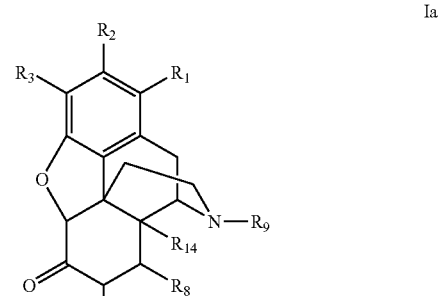

Ia

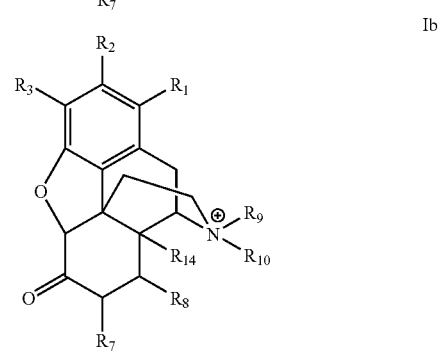

Ib

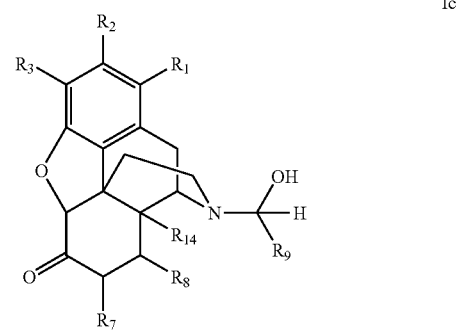

Ic

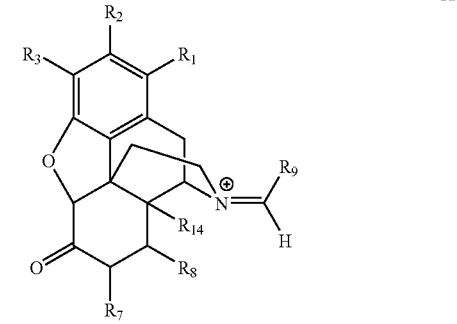

Id

In addition, as used herein, the symbol ">" is used in conjunction with the nitrogen atom to illustrate the two covalent bonds that bind the nitrogen atom to the morphinan.

In one embodiment of the present invention, the morphinan corresponds to Formula (Ia) where $R_9$ is hydrogen or substituted or unsubstituted $C_{1-8}$ alkyl, $C_{2-8}$ alkenyl, aryl, heterocyclo, or acyl. Typical acyl groups include, but are not limited to, esters, amides, and carbamates. The optical activity, with respect to the rotation of polarized light, of the morphinan having Formula (Ia) may be (+) or (−). Furthermore, the configuration of carbons C-5, C-13, C-14, and C-9, respectively, of the Formula (Ia) compound may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule.

In one example of this embodiment, $R_9$ is hydrogen, $C_{1-8}$ alkyl, $C_{2-8}$ alkenyl, aryl, heterocyclo, ester, amide, or carbamate. In a more restrictive example, $R_9$ is hydrogen, methyl, ethyl, propyl, cyclopropyl, cyclopropylmethyl, butyl, isobutyl, t-butyl, cyclobutyl, cyclobutylmethyl, methylcarbonyl, ethylcarbonyl, propylcarbonyl, cyciopropylcarbonyl, butylcarbonyl, isobutylcarbonyl, cyclobutylcarbonyl, or allyl; preferably, hydrogen, methyl, ethyl, cyclopropylmethyl, cyclobutylmethyl, cyclopropylcarbonyl, or cyclobutylcarbonyl. In a preferred example of this embodiment, the 6-keto morphinan is noroxymorphone; that is, $R_1$, $R_2$, $R_7$, and $R_8$ are hydrogen; $R_{14}$ is β-hydroxy; and $R_9$ is hydrogen. For reference, the structure of noroxymorphone is as follows:

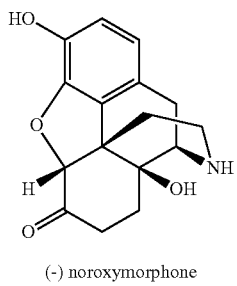

(−) noroxymorphone

In another embodiment the morphinan corresponds to Formula (Ib) where $R_9$ and $R_{10}$ are independently hydrogen or substituted or unsubstituted $C_{1-8}$ alkyl, $C_{2-8}$ alkenyl, aryl, heterocyclo, or acyl. Typical acyl groups include, but are not limited to, esters, amides, and carbamates. The optical activity of the morphinan having Formula (Ib) may be (+) or (−). In embodiments in which $R_9$ and $R_{10}$ are identical, the configuration of the stereogenic carbons, C-5, C-13, C-14, and C-9, respectively, may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule. Whereas, in embodiments in which $R_9$ and $R_{10}$ are different, the configuration of the stereogenic centers, C-5, C-13, C-14, C-9, and N-17, respectively, may be RRRRR, RRRRS, RRSRR, RRSRS, RRRSR, RRRSS, RRSSR, RRSSS, RSRRR, RSRRS, RSSRR, RSSRS, RSRSR, RSRSS, RSSSR, RSSSS, SRRRR, SRRRS, SRSRR, SRSRS, SRRSR, SRRSS, SRSSR, SRSSS, SSRRR, SSRRS, SSSRR, SSSRS, SSRSR, SSRSS, SSSSR, or SSSSS, provided that the C-15 and the C-16 carbons are both either on the alpha face of the molecule or the beta face of the molecule.

In one example of this embodiment, $R_9$ and $R_{10}$ are independently hydrogen, $C_{1-8}$ alkyl, $C_{2-8}$ alkenyl, aryl, heterocyclo, ester, amide, or carbamate. In a more restrictive example, $R_9$ and $R_{10}$ are independently hydrogen, methyl, ethyl, propyl, cyclopropyl, cyclopropylmethyl, butyl, isobutyl, t-butyl, cyclobutyl, cyclobutylmethyl, methylcarbonyl, ethylcarbonyl, propylcarbonyl, cyclopropylcarbonyl, butylcarbonyl, isobutylcarbonyl, cyclobutylcarbonyl, or allyl; preferably, hydrogen, methyl, ethyl, cyclopropylmethyl, cyclobutylm-
ethyl, cyclopropylcarbonyl, or cyclobutylcarbonyl. In one preferred example, $R_9$ is cyclopropylmethyl and $R_{10}$ is methyl. In another preferred example, $R_9$ is $C_{1-8}$alkyl and $R_{10}$ is hydrogen.

In still another embodiment, the 6-keto morphinan corresponds to Formula (Ic) where $R_9$ is hydrogen, or substituted or unsubstituted $C_{1-8}$ alkyl, $C_{2-8}$ alkenyl, aryl, heterocyclo, or acyl. Typical acyl groups include, but are not limited to, esters, amides, and carbamates. The optical activity of the morphinan having Formula (Ic) may be (+) or (−). In embodiments in which $R_9$ is hydrogen or hydroxy, the configuration of the chiral carbons, C-5, C-13, C-14, and C-9, respectively, may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule. In embodiments in which $R_9$ is not hydrogen or hydroxy, the carbon (C-18) attached to N-17 is also chiral, and thus, the configuration of C-5, C-13, C-14, C-9, and C-18, respectively, may be RRRRR, RRRRS, RRSRR, RRSRS, RRRSR, RRRSS, RRSSR, RRSSS, RSRRR, RSRRS, RSSRR, RSSRS, RSRSR, RSRSS, RSSSR, RSSSS, SRRRR, SRRRS, SRSRR, SRSRS, SRRSR, SRRSS, SRSSR, SRSSS, SSRRR, SSRRS, SSSRR, SSSRS, SSRSR, SSRSS, SSSSR, or SSSSS, provided that the C-15 and the C-16 carbons are both either on the alpha face of the molecule or the beta face of the molecule.

In one example of this embodiment, $R_9$ is hydrogen, $C_{1-8}$ alkyl, $C_{2-8}$ alkenyl, aryl, heterocyclo, ester, amide, or carbamate. In a more restrictive example, $R_9$ is hydrogen, methyl, ethyl, propyl, cyclopropyl, cyclopropylmethyl, butyl, isobutyl, t-butyl, cyclobutyl, cyclobutylmethyl, methylcarbonyl, ethylcarbonyl, propylcarbonyl, cyclopropylcarbonyl, butylcarbonyl, isobutylcarbonyl, cyclobutylcarbonyl, or allyl; preferably, hydrogen, methyl, ethyl, cyclopropyl or cyclobutyl.

In another embodiment, the 6-keto morphinan corresponds to Formula (Id) where $R_9$ is hydrogen, or substituted or unsubstituted $C_{1-8}$ alkyl, $C_{2-8}$ alkenyl, aryl, heterocyclo, or acyl. Typical acyl groups include, but are not limited to, esters, amides, and carbamates. The optical activity of the morphinan having Formula (Id) may be (+) or (−), and the configuration of the chiral carbons, C-5, C-13, C-14, and C-9, respectively, may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule.

In one example of this embodiment, the imine is converted to the corresponding tertiary amino moiety under the same conditions as the conversion of the 6-keto to the 6-α-hydroxy moiety. Accordingly, both groups may be reduced in tandem in a one pot reaction. In one example of this embodiment, $R_9$ is hydrogen, $C_{1-8}$alkyl, $C_{2-8}$alkenyl, aryl, heterocyclo, ester, amide, or carbamate, In a more restrictive example, $R_9$ is hydrogen, methyl, ethyl, propyl, cyclopropyl, cyclopropylmethyl, butyl, isobutyl, t-butyl, cyclobutyl, cyclobutylmethyl, methyloarbonyl, ethylcarbonyl, propylcarbonyl, cyclopropylcarbonyl, butylcarbonyl, isobutylcarbonyl, cyclobutylcarbonyl, or allyl; preferably, hydrogen, methyl, ethyl, cyclopropyl or cyclobutyl, In one preferred example, $R_9$ is cyclobutyl.

For any of the above embodiments where the morphinan corresponds to Formula (I) and $Z_1$ is $>N(R_9)$, $>N^+(R_9)(R_{10})$, $>NCH(OH)(R_9)$, or $>N^+=CH(R_9)$, $R_3$ is typically —$OR_{311}$ where $R_{311}$ is hydrogen, alkyl, acyl, alkaryl, aryl, or a hydroxy protecting group. In one example of this embodiment, $R_{311}$ is hydrogen, $C_{1-8}$ alkyl, aryl, $C_{1-8}$ alkyl-C(O)—, aryl-C(O)—, $C_{1-8}$ alkyl-OC(O)—, or aryl-OC(O)—. In another example, $R_{311}$ is hydrogen or $C_{1-8}$ alkyl; preferably hydrogen or methyl. In a preferred example, $R_{311}$ is hydrogen.

In one embodiment in which the morphinan corresponds to Formula (I), $R_1$, $R_2$, $R_7$, and $R_8$ are hydrogen. In an alternative embodiment, at least one of $R_1$, $R_2$, $R_7$, and $R_8$ is other than hydrogen; for example, $R_1$ may be hydrocarbyl, halo, or —$OR_{111}$ where $R_{111}$ is hydrogen, alkyl, acyl, alkaryl, aryl, or a hydroxy protecting group.

When a 6-keto morphinan corresponding to Formula (I) is reduced in the presence of a ruthenium, rhodium, or iridium asymmetric catalyst and a hydrogen source in accordance with the process of the present invention, the resulting 6-hydroxy morphinan corresponds to Formula (II):

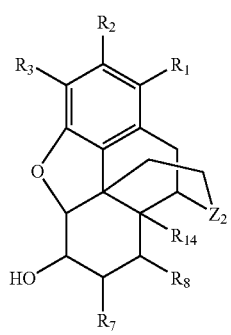

(II)

wherein $R_1$, $R_2$, $R_3$, $R_7$, $R_8$, $R_9$, $R_{10}$, and $R_{14}$ are as previously defined for Formula (I) and $Z_2$ is $Z_1$ when $Z_1$ corresponds to Formula (Ia) or (Ib) or $Z_2$ is >$NCH_2(R_9)$ when $Z_1$ corresponds to Formula (Ic) or (Id).

The optical activity of a 6-hydroxy morphinan corresponding to Formula (II) may be (+) or (−), and the configuration of the chiral carbons, C-6, C-5, C-13, C-14, and C-9, respectively, may be RRRRR, RRRRS, RRSRR, RRSRS, RRRSR, RRRSS, RRSSR, RRSSS, RSRRR, RSRRS, RSSRR, RSSRS, RSRSR, RSRSS, RSSSR, RSSSS, SRRRR, SRRRS, SRSRR, SRSRS, SRRSR, SRRSS, SRSSR, SRSSS, SSRRR, SSRRS, SSSRR, SSSRS, SSRSR, SSRSS, SSSSR, or SSSSS, provided that the C-15 and the C-16 carbons are both either on the alpha face of the molecule or the beta face of the molecule, and the 6-hydroxy is on the alpha face of the molecule.

Exemplary morphinan (II) products include nalbuphine, oxymorphol, oxycodol, noroxymorphol, naloxol, naltrexol, hydrocodol, and hydromorphol:

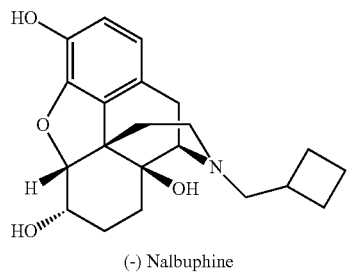

(−) Nalbuphine

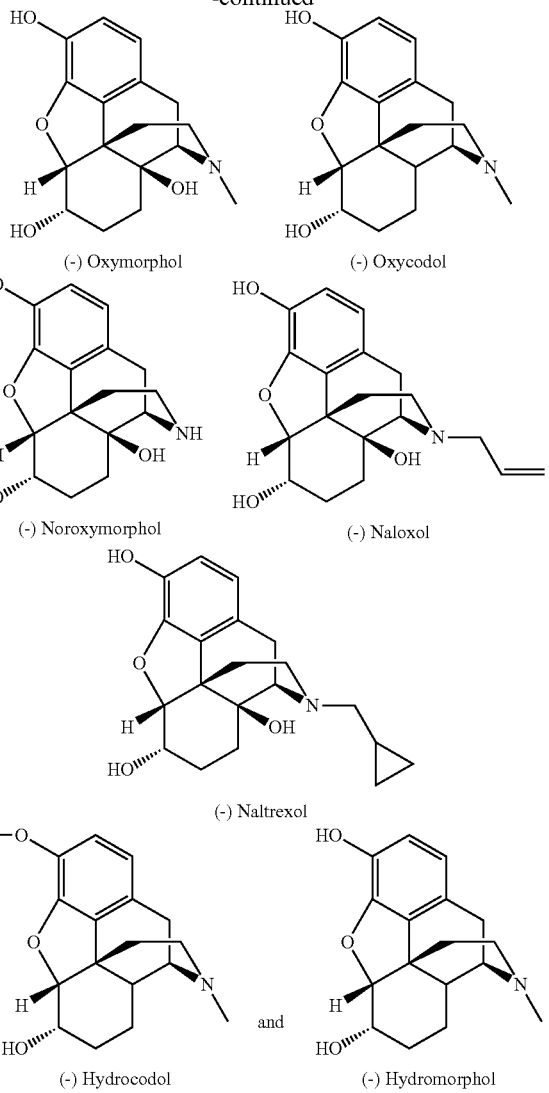

Ruthenium, Rhodium, or Iridium Asymmetric Catalysts

Generally, the ruthenium, rhodium, or iridium asymmetric catalysts of the present invention facilitate enantioselective reductions of the 6-keto moiety of a morphinan to the 6-α-hydroxy epimer. Further, these catalysts, under certain conditions described herein, may also facilitate the reductions of the N-imine ($Z_1$⇒$N^+$=$CH(R_9)$) or the hemiaminal ($Z_1$⇒$NCH(OH)(R_9)$). In general, the asymmetric catalysts of the present invention comprise (a) a metal source consisting of a ruthenium complex, a rhodium complex, an iridium complex, or a combination thereof and (b) one or more chiral ligands. Typically, the ratio of metal to chiral ligand is about 1:1. In one example, the metal source is a ruthenium complex or a rhodium complex. In another example, the metal source is dichloro(arene)Ru(II) dimer, dichloro(pentamethylcyclopentadienyl)Rh(II) dimer, BINAP-Ru (II) diacetate, BINAP-Ru (II) dichloride, BINAP-Ru (II) dibromide, BINAP-Ru (II) diiodide, [RuCl((R or S)BINAP)($C_6H_6$)]Cl, or dichloro(pentamethylcyclopentadienyl)iridium (III) dimer.

Typically, the asymmetric catalysts of the present invention comprise ruthenium, rhodium, iridium, or a combination thereof complexed with bidentate, chiral ligands using nitrogen, oxygen, or phosphorous donor atoms as more fully described in, for example, U.S. Pat. No. 5,693,820 (Helmchen et al.) and R. Noyori et al., *Asymmetric Catalysts by Architechtural and Functional Molecular Engineering: Practical Chemo-and Stereoselective Hydrogenation of Ketones*, Agew. Chem. Int. Ed. 2001, 40, pp. 40-73. These catalysts are sometimes referred to as Noyori catalysts. In one example, the chiral ligand of the present asymmetric catalysts corresponds to Formulae (670), (680), (690), or (700)

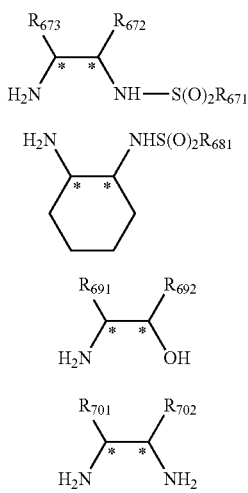

wherein $R_{671}$, $R_{672}$, $R_{673}$, $R_{681}$, $R_{691}$, $R_{692}$, $R_{701}$, and $R_{702}$ are independently alkyl or aryl and wherein $R_{691}$ and $R_{692}$ of Formula (690) and $R_{701}$ and $R_{702}$ of Formula (700), and the carbon atoms to which they are attached, may optionally form a cyclic or bicyclic compound. In the above structures, the "*" indicates a chiral carbon atom. The configuration of the chiral carbons of the asymmetric catalyst may be RR, RS, SR, or SS.

In one embodiment, the ligand corresponds to Formula (670) and $R_{672}$ and $R_{673}$ are each phenyl and $R_{671}$ is aryl. In another example of this embodiment, $R_{671}$ is tolyl, mesityl, or naphthyl. In an alternative embodiment, the ligand corresponds to Formula (680) and $R_{681}$ is tolyl, mesityl, 2,4,6-triisopropylphenyl, or naphthyl. In another example, the ligand corresponds to Formula (690) and $R_{691}$ and $R_{692}$ are hydrogen thus forming the compound, aminoethanol. In an alternative example, the ligand corresponds to Formula (690) and $R_{691}$ and $R_{692}$ are selected to form the following compound:

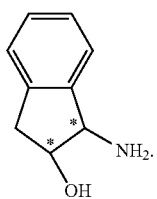

In another embodiment, the ligand corresponds to Formula (700) and $R_{701}$ and $R_{702}$ are hydrogen thus forming the compound, ethylenediamine.

In a preferred example, the ligand is (1S,2S)-(+)-N-4-toluenesulfonyl-1,2-diphenylethylene-1,2-diamine, (1R,2R)-(−)-N-4-toluenesulfonyl-1,2-diphenylethylene-1,2-diamine, dl-N-tosyl-1,2-diphenylethylenediamine, N-tosyl-1,2-diphenylethylenediamine, N-tosyl-1,2-ethylenediamine, or N-tosyl-1,2-diaminocyclohexane.

Examples of active ruthenium and rhodium asymmetric catalysts of the present invention include the following:

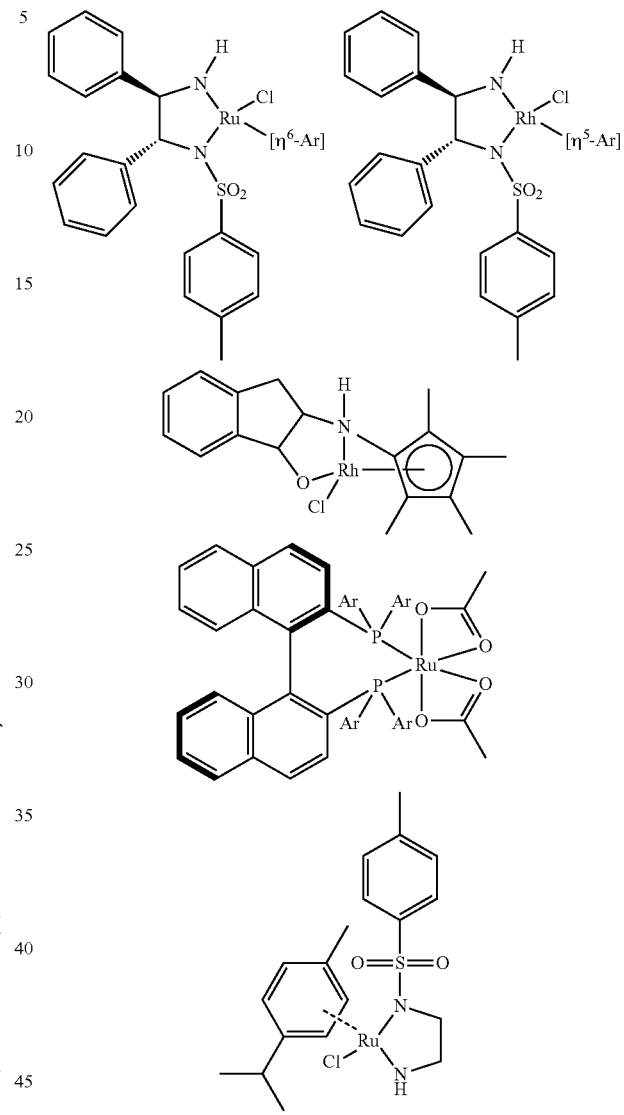

Chemical Formula: $C_{20}H_{29}ClN_2O_2RuS$
Exact Mass: 498.1
Molecular Weight: 498

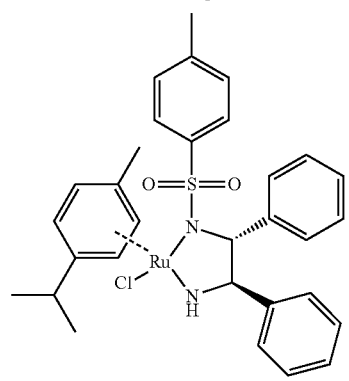

Chemical Formula: $C_{32}H_{37}ClN_2O_2RuS$
Exact Mass: 650.1
Molecular Weight: 650.2

-continued

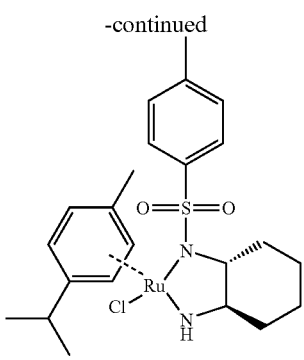

Chemical Formula: $C_{24}H_{35}ClN_2O_2RuS$
Exact Mass: 552.1
Molecular Weight: 552.1

Hydrogen Source

The hydrogen source of the present process is any hydrogen source known to those skilled in the art. Methods of hydrogenation include in situ hydrogen transfer and high pressure hydrogenation. In one example, the hydrogen source is hydrogen gas, which has been shown to be effective for the reduction of 6-keto morphinans. To accomplish the reduction using this source, however, special reactors are required. On a preparative scale, this poses safety challenges. An alternative to hydrogen gas is producing hydrogen in situ through hydrogen transfer methods. By producing the hydrogen source in situ, the pressures of standard hydrogenations (sometimes at 100 atoms $H_2$) are avoided, thereby allowing for a safer preparation environment.

Generally, the hydrogen source for the process of the present invention is selected from isopropanol, formic acid, organic or inorganic salts of formic acid, or a combination thereof. In some instances, a small amount of base may be used to activate the catalyst. For example, in isopropanol, KOH is often used as an activator. In other examples, triethylamine may be used. In one example, the hydrogen source comprises an organic or inorganic salt of formic acid, preferably, the triethylamine salt of formic acid. In a preferred example, the hydrogen source is about a 5:2 mixture of formic acid to triethylamine.

Solvent

Typically, the solvent for the process of the present invention is selected from a nitrile (e.g., acetonitrile, propionnitrile), tetrahydrofuran (THF), an alcohol (e.g., methanol, ethanol, etc.), a halocarbon (e.g., a chloroalkyl such as dichloromethane, chloroform, 1,2-dichloroethane, or tetrachloroethylene), dimethylformamide (DMF), dimethylacetamide (DMAc), N-methyl pyrrolidinone (NMP), an alkyl acetate (e.g., ethyl acetate or propyl acetate), toluene, or a combination thereof. In a more restrictive example, the solvent is acetonitrile, DMAc or a combination of acetonitrile and methanol.

Generally, the reaction converting the 6-keto to the 6-α-hydroxy group may be conducted at a temperature range from ambient temperature (~20° C.) to about 120° C. Although the reaction will proceed at elevated temperatures, higher temperatures tend to erode the desired epimeric ratio. In one example, the reaction is carried out at temperature range of about 0° C. to about 80° C., preferably from about room temperature (~25° C.) to about 40° C.

Reaction Schemes

The process for the conversion of the 6-keto group to the 6-α-hydroxy group may yield an end product morphinan or an intermediate morphinan, which can be modified in one or more additional steps to achieve the desired end compound. For illustrative purposes, the following schemes depict various synthetic routes for the synthesis of 6-α-hydroxy morphinans. As shown below, the process of converting a 6-keto morphinan to the corresponding 6-α-hydroxy morphinan can occur at any step of the overall process in the preparation of the desired morphinan.

Typically, the N-imine morphinan (Id) and the hemiaminal morphinan (Ic) of the present invention are synthesized by reacting a nor-morphinan with an aldehyde having the formula $R_9CH(O)$ as illustrated in Scheme 1. These two morphinans are then converted to the end product morphinan (II) according to the process of the present invention.

Scheme 1

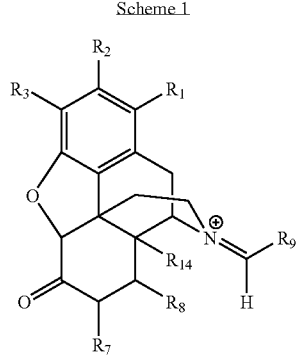

Id

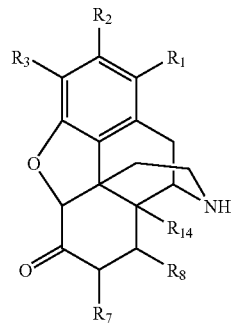

STEP 1
aldehyde [CH(O)—R$_9$]
solvent

STEP 2
asymmetric catalyst
hydrogen source

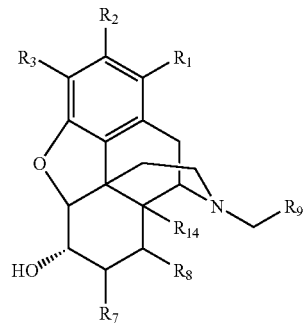

II

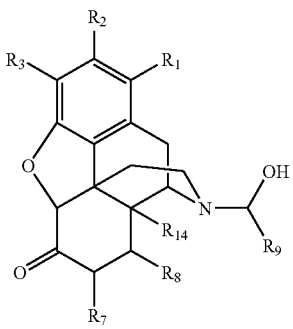

Ic

For Reaction Scheme 1, $R_1$, $R_2$, $R_3$, $R_7$, $R_8$, $R_{14}$, and $R_9$ are as previously defined. In Step 1, an imine nitrogen and/or hemiaminal is formed by reacting the 6-keto morphinan with an aldehyde of the formula CH(O)—R$_9$. The aldehyde is typically introduced in an amount ranging from about 1.0 to about 1.25 equivalents of aldehyde per equivalent of 6-keto morphinan. The solvent system for this step typically comprises an organic solvent, such as methanol, acetonitrile, toluene, ethyl acetate, or a combination thereof. The Step 1 reaction may be carried out, for example, at a temperature range of about room temperature (25° C.) to about reflux. Preferably, the reaction is carried out at about room temperature (25° C.) over a period of about 1 to about 5 hours, typically about 3 hours. An azeotropic distillation step may be added to increase the reaction rate of imine formation.

In Step 2, an asymmetric reduction using hydrogen transfer of the 6-keto and imine and/or hemiaminal is carried out. Typically, for this type of reaction, the N-imine morphinan (Id) and the hemiaminal morphinan (Ic) are in equilibrium. When treated with a ruthenium, rhodium, or iridium asymmetric catalyst and a hydrogen source, as described herein, the N-imine moiety is converted to the corresponding tertiary amino group and the hydroxy group of the hemiaminal moiety is removed thereby forming the 6-α-hydroxy morphinan product (II). Without being bound to any particular theory, it is believed that the product (II) is predominantly, if not entirely, formed from the N-imine morphinan (Id). It may be that the reduction of the N-imine morphinan to the product, coupled with the equilibrium formed with the hemiaminal morphinan, is the driving force behind the reaction. That is, the more N-imine morphinan is reduced to product, the more hemiaminal morphinan converts to the N-imine morphinan to maintain balance in the equilibrium. Sufficient evidence for this theory, however, is lacking. It is known, that when the mixture of N-imine and hemiaminal morphinans is reacted with a ruthenium, rhodium, or iridium asymmetric catalyst and a hydrogen source, the end product forms in high yield.

While the keto, imine, and hemiaminal reductions can be conducted separately under certain conditions, it is generally advantageous to perform a tandem, one pot reaction to reduce all groups. For the one pot reaction, the catalyst is generally loaded at about a 1/50 to about a 1/1000 loading ratio. The hydrogen source can be any of those previously discussed. In one preferred example, the hydrogen source is 1 to 8 equivalents of 2:5 mixture of triethylamine to formic acid (NEt$_3$/HCO$_2$H). If large amounts of aldehydes are used, an increased amount of NEt$_3$/HCO$_2$H may be required. The solvent system for this step typically comprises a halocarbon, methanol, acetonitrile, ethyl acetate, propyl acetate, THF, DMF, DMAc, toluene, or a combination thereof. The substrate to solvent concentration is typically about 1:1 to about 1:10, preferably about 1:5. The temperature range for this one pot synthetic reaction is typically from about room temperature (25° C.) to about 40° C. At room temperature, the reaction typically takes from about 12 hours to about 72 hours. The reaction time, however, will depend upon the catalyst loading ratio and reaction temperature.

Scheme 2

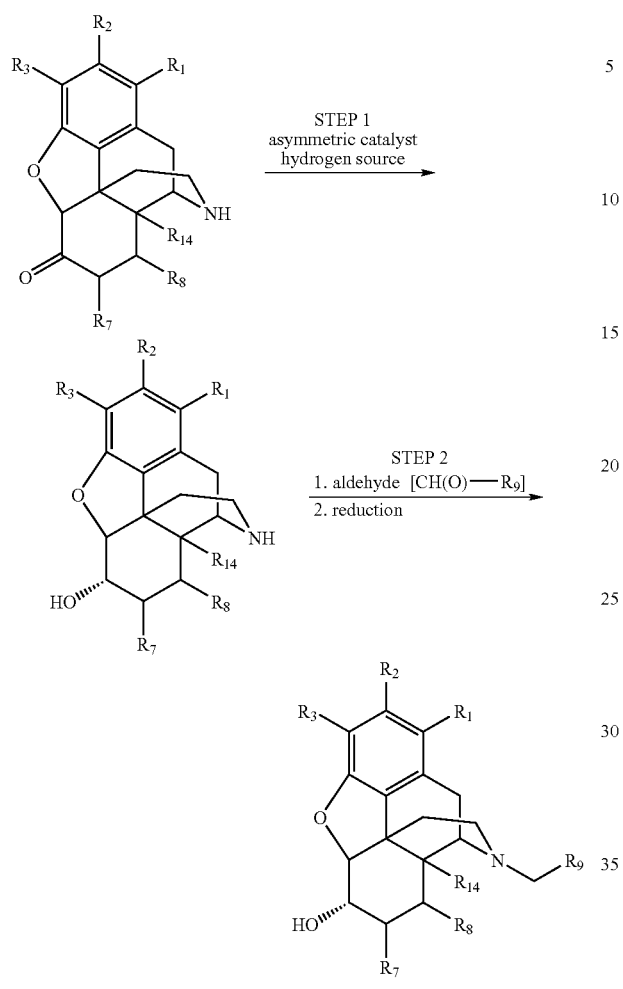

For Reaction Scheme 2, $R_1$, $R_2$, $R_3$, $R_7$, $R_8$, $R_9$, and $R_{14}$ are as previously defined for morphinans of Formula (I). In contrast to Scheme 1, the 6-keto group of Scheme 2 is converted to the 6-α-hydroxy group prior to N-alkylation. Generally, the substrate to solvent ratio is from about 1:2 to about 1:20, preferably about 1:4 to about 1:5. The hydrogen source can be any of those previously discussed. In one preferred example, the hydrogen source is 1 to 5 equivalents of a 2:5 mixture of triethylamine to formic acid ($NEt_3/HCO_2H$), plus an additional equivalent to form a salt with the morphinan nitrogen, which increases solubility of the morphinan. Other salts that may be used include the methanesulfonate, acetate, and hydrochloride salt. These salts, however, may react at a slower rate. The catalyst is generally loaded at about a 1/50 to about a 1/1000 loading ratio on a molar basis. Typically, this reaction occurs in a temperature range of about room temperature (25° C.) to about 40° C. Above 40° C., the desired epimeric ratio begins to rapidly erode; that is, there is increased formation of the 6-β-epimer. The more dilute the solvent, the longer the reaction time at room temperature.

In Step 2, the morphinan nitrogen is alkylated by reacting the morphinan with an aldehyde of the formula CH(O)—$R_9$ in a solvent. The solvent for Step 2 is typically an organic solvent, such as acetonitrile, ethyl acetate, DMF, DMAc, NMP, THF, etc, or a combination thereof. This reaction may occur at a temperature range of about −20° C. to reflux, depending on the solvent. After the nitrogen is alkylated, the morphinan is reduced using procedures known in the art to form the N-alkylated morphinan end compound. Typically, for this reduction, normal main group hydride reducing agents are used (e.g., boranes, lithium aluminum hydrides, hydrogen in the presence of a catalyst). During this process, if the 3-hydroxy group was previously acylated, it is reduced back to the phenol.

Scheme 3

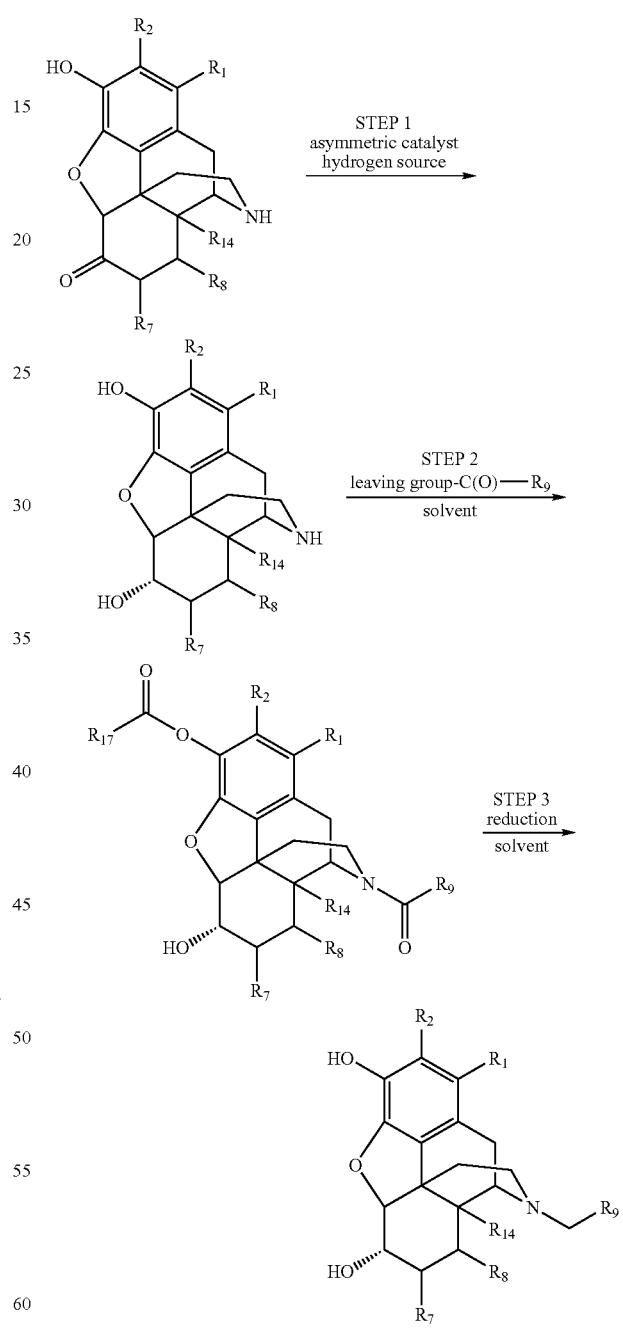

For Reaction Scheme 3, $R_1$, $R_2$, $R_7$, $R_8$, $R_9$, and $R_{14}$ are as previously defined. For illustration purposes, $R_3$ is hydroxy. Scheme 3 utilizes an acylation reduction protocol. In Step 1, the 6-keto morphinan is converted to the corresponding 6-α-hydroxy morphinan via the process described above. Accordingly, the catalyst, hydrogen source, solvent, and reaction conditions for Step 1 are any of those previously discussed.

In Step 2, the morphinan nitrogen is acylated using, for example, an alkyl carbonyl chloride. Other leaving groups include chloride, bromide, and heterocyclics (e.g., imidazole, triazole, hydroxybenztriazole, etc.). Solvents for this reaction include, for example, halocarbons, toluene, THF, ether, ethyl acetate, DMF, DMAc, NMP, and combinations thereof. To remove the hydroacid produced from the acid halide and amine reaction, typically a base, organic or inorganic, is used. Also, the hydroacid may be removed, under conditions known to those skilled in the art, by bubbling it out of solution. Further, coupling reagents may also be used as understood by those skilled in the art (e.g., carboxylic acid and dicyclohexylcarbodiimide (DCC), then amine or carboxylic acid and carbonyldiimidazole (CDI), then amine). As shown in this particular scheme, the 3-hydroxy group is also acylated. If the starting morphinan had a 3-substituent other than hydroxy, the 3-position would not likely be acylated. Typically, this reaction occurs at a temperature range of about 0° C. to about room temperature (25° C.); however, higher temperatures are also acceptable.

In Step 3, the 3,14 bis acylated morphinan intermediate undergoes reduction with main group hydride reagents, for example, lithium aluminum hydride, boranes, etc. In this process, the phenolic ester at the 3-position is reduced back to the phenol. Solvents for this reaction step include THF and toluene. The temperature for this reaction is typically between 0° C. and reflux.

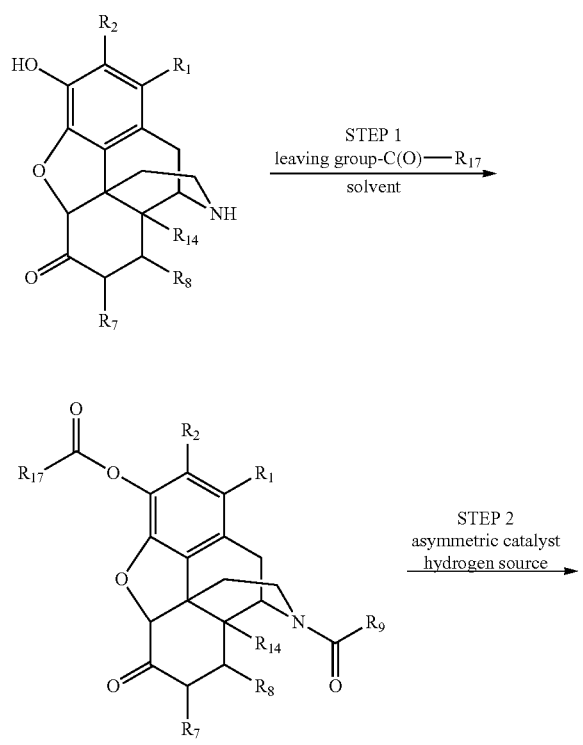

Scheme 4

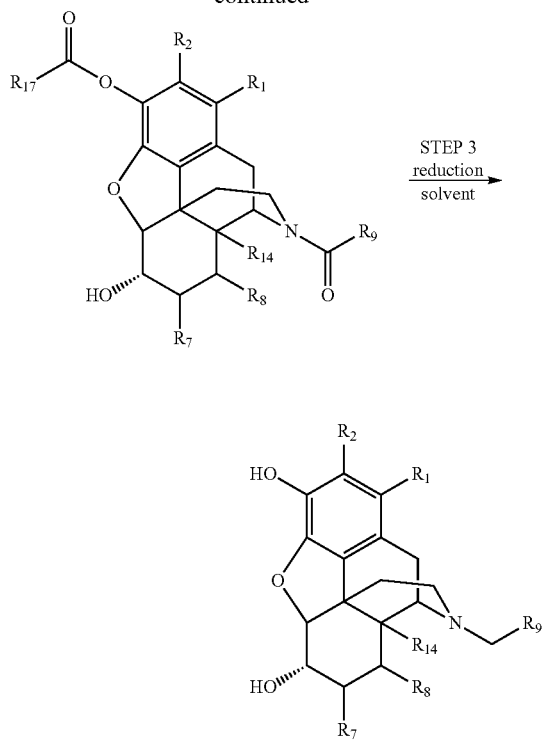

For Reaction Scheme 4, $R_1$, $R_2$, $R_7$, $R_8$, $R_9$, and $R_{14}$ are as previously defined. For illustration purposes, $R_3$ is hydroxy. Like Scheme 3, an acylation reduction protocol is depicted in Scheme 4. The acylation of the 3-hydroxy and the nitrogen, however, occur prior to the conversion of the 6-keto group to the 6-α-hydroxy group.

In Step 1, the nitrogen is acylated using, for example, an alkyl carbonyl chloride. Other leaving groups, such as p-toluenesulfonate, mesylate, etc. may be used in combination with internal Finkelstein condensation. Triflate may also be used under certain conditions known to those in the art. Solvents for this reaction include, for example, THF, ether, ethyl acetate, DMF, DMAc, and NMP. As shown in this particular scheme, the 3-hydroxy group is also acylated. If the starting morphinan had a 3-substituent other than hydroxy, the 3-position would not likely be acylated. Typically, this reaction occurs at a temperature range of about −78° C. to about room temperature (25° C.); however, higher temperatures are also acceptable.

In Step 2, the 6-keto group of the 3,14 bis acylated morphinan intermediate is converted to the 6-α-hydroxy intermediate via the process previously described.

In Step 3, the 6-α-hydroxy intermediate is reduced with main group hydride reagents, for example, lithium aluminum hydride, boranes, etc. In this process, the phenolic ester at the 3-position is reduced back to the phenol at the same time that the acyl group on the nitrogen is converted to the corresponding alkyl group.

Scheme 5

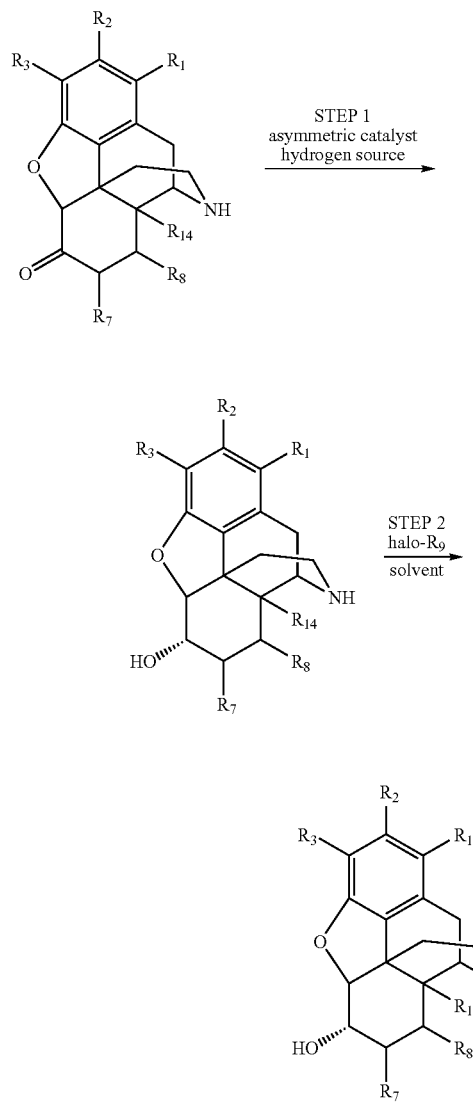

For Reaction Scheme 5, $R_1$, $R_2$, $R_3$, $R_7$, $R_8$, $R_9$, and $R_{14}$ are as previously defined. Scheme 5 depicts a nitrogen alkylation reaction to form the final product.

In Step 1, the 6-keto morphinan is converted to the corresponding 6-α-hydroxy morphinan via the process previously described.

Step 2 of Scheme 5 depicts a nitrogen alkylation reaction using, for example, a haloalkyl group. In one example, the haloalkyl group is an alkyl bromide. Other leaving groups, such as chloride, p-toluenesulfonate, mesylate, etc. may be used in combination with internal Finkelstein condensation. Triflate may also be used under certain conditions known to those in the art. Depending on the base (organic or inorganic) used and the equivalence of the reagent in the alkylation, 3 and/or 14 alkylation can result. The 3,N-bis alkylated by-product normally occurs when excess alkylating agent is used. Typical solvents for this reaction include acetone, acetonitrile, ethyl acetate, DMF, DMAc, NMP, DMSO, etc.

Scheme 6

For Reaction Scheme 6, $R_1$, $R_2$, $R_3$, $R_7$, $R_8$, $R_9$, and $R_{14}$ are as previously defined. Step 1 of Scheme 6 depicts a nitrogen alkylation reaction using, for example, a haloalkyl group. In one example, the haloalkyl group is an alkyl bromide. Other leaving groups, such as chloride, p-toluenesulfonate, mesylate, etc. may be used in combination with internal Finkelstein condensation. Triflate may also be used under certain conditions known to those in the art. Depending on the base (organic or inorganic) used and the equivalence of the reagent in the alkylation, 3 and/or 14 alkylation can result. The 3,N-bis alkylated by-product normally occurs when excess alkylating agent is used. Typical solvents for this reaction include acetone, acetonitrile, ethyl acetate, DMF, DMAc, NMP, DMSO, etc.

In Step 2, the 6-keto morphinan is converted to the corresponding 6-α-hydroxyl morphinan via the previously described process.

DEFINITIONS

The compounds described herein may have asymmetric centers. Compounds of the present invention containing an asymmetrically substituted atom may be isolated in optically active or racemic form. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R_1$, $R_1O$—, $R_1R_2N$—, or $R_1S$—, $R_1$ is hydrocarbyl, heterosubstituted hydrocarbyl, or heterocyclo, and $R_2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "Finkelstein reaction" as used herein describes a halide (leaving group) exchange as explained, for example, in "March's Advanced Organic Chemistry, Fifth Edition", John Wiley & Sons, 2001, pages 517-518. This reaction can be used, for example, to prepare highly reactive alkyl iodides in situ by mixing a source of iodide (normally a sodium or potassium salt) with an alkyl chloride or bromide. Tosylates, mesylates, etc can also be used in this type of reaction.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "hydroxy protecting group" as used herein denote a group capable of protecting a free hydroxy group ("protected hydroxy") which, subsequent to the reaction for which protection is employed, may be removed without disturbing the remainder of the molecule. Exemplary hydroxy protecting groups include oxygen protecting groups of alkylsulfonates and arylsulfonates, ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups for the hydroxy group and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

As used herein, DCBC is dicyclobutylcarbonyl and BINAP is 2,2'-bis(diphenylphosphino)-1,1'-binaphthyl, THF is tetrahydrofuran, DMF is dimethylformamide, DMAc is dimethylacetamide, NMP is N-methyl pyrrolidinone, and DMSO is dimethyl sulfoxide.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following non-limiting examples are provided to further illustrate the present invention.

Example 1

Synthesis of 6-α-Naltrexol

Noroxymorphone (2.12 g, 7.4 mmole) was added to acetonitrile (9 mL). Cyclopropane-carboxaldehyde (1.03 g, 14.8 mmol, 1.10 mL) was added and the slurry stirred for 2 hours at room temperature. At that time, a 5 to 2 mixture of 98% formic acid/triethylamine [prepared by adding 98% formic acid (4.25 g, 92.3 mmol, 3.48 mL) to triethylamine (3.73 g, 37 mmol, 5.14 mL) in 9 mL of acetonitrile] was added. Dichloro(p-cymene)ruthenium (II) dimer (21 mg, 0.034 mmol) was added followed by addition of (1S,2S)-(+)-N-tosyl-diphenylethylene diamine (25 mg, 0.069 mmol). The reaction was then purged by nitrogen gas (argon) for 10 minutes. After the nitrogen purge, a flow of nitrogen was allowed to pass over the reaction. The reaction was stirred for 24 hours at room temperature. HPLC analysis indicated the reaction was complete (6-α-Naltrexol: 99.1%, 6-β-Naltrexol: 0.9%). Approximately 80% of the acetonitrile was removed under reduced pressure. Distilled water (10 mL) was then added and a white precipitate formed. Filtration of the white precipitate and washing with distilled water yielded the product (2.32 g, 92% yield).

Example 2

Synthesis of 6-α-Oxymorohol

Oxymorphone (1.20 g, 4.17 mmole) was added to acetonitrile (5.0 mL). Paraformaldehyde (0.25 g, 8.33 mmol) was then added and the slurry was stirred for 16 hours at room temperature. At that time, a 5 to 2 mixture of 98% formic acid/triethylamine [prepared by adding 98% formic acid (2.40 g, 52.1 mmol, 1.97 mL) to triethylamine (2.11 g, 20.8 mmol, 2.91 mL) in 5.0 mL of acetonitrile) was added. Dichloro(p-cymene)ruthenium (II) dimer (12.0 mg) was added followed by the addition of (1S, 2S)-(+)-N-tosyl-diphenylethylene diamine (15 mg). The reaction was purged by nitrogen gas (argon) for 30 minutes. After the nitrogen purge, a flow of nitrogen was allowed to pass over the reaction. The reaction was stirred for 24 hours at room temperature. HPLC analysis indicated that the reaction was complete (6-α-Oxymorphol: 98.9%, 6-β-Oxymorphol: 0.9%). The mixture was then evaporated to a thick oil. 5.0 mL of acetonitrile was then added and stirred at room temperature for 6 hours where a precipitate formed. The precipitate was removed by filtration and washed with 2.0 mL cold (5° C.) acetonitrile. The precipitate was dried yielding the product (1.15 g, 92% yield).

Example 3

Synthesis of Nalbuphine

Noroxymorphone (2.26 g, 7.86 mmole) was added to acetonitrile (15.0 mL). Cyclobutanecarboxaldehyde (1.32 g, 15.6 mmol) was then added and the slurry stirred for 3 hours at room temperature. At that time, a 5 to 2 mixture of 98% formic acid/triethylamine [prepared by adding 98% formic acid (4.53 g, 98.4 mmol, 3.71 mL) to triethylamine (3.98 g, 39.9 mmol, 5.48 mL) in 15.0 mL of acetonitrile) was added. Dichloro(p-cymene)ruthenium (II) dimer (23 mg) was added followed by addition of (1S,2S)-(+)-N-tosyl-diphenylethylene diamine (20 mg). The reaction was then purged by nitrogen gas (argon) for 30 minutes. After the nitrogen purge, a flow of nitrogen was allowed to pass over the reaction. The reaction was then stirred for 24 hours at room temperature. HPLC analysis indicated that the reaction was complete (Nalbuphine: 98.7%, 6-β-Naltrexol: 1.3%). The mixture was then evaporated to a thick oil. 2.0 mL of acetonitrile was added and stirred at room temperature for 1 hour where a precipitate formed. The precipitate was removed by filtration and washed with 2.0 mL cold (5° C.) acetonitrile. The precipitate was dried yielding the product (2.60 g, 92.5% yield).

Example 4

Synthesis of 6-α-Oxymorphol from Oxymorphone

Triethylamine (3.88 g, 38.4 mmol, 5.3 mL) and 15 mL of dry acetonitrile were added into a round bottom flask. To this mixture was added 98% formic acid (4.95 g, 10.75 mmol, 4.05 mL). The reaction exothermed and was stirred for 30 minutes until the temperature reached room temperature. Oxymorphone (3.50 g, 11.6 mmol) was added. To this slurry was added Dichloro(p-cymene)ruthenium (II) dimer (35 mg, 0.057 mmol) followed by (1S,2S)-(+)-N-tosyl-diphenylethylene diamine (42 mg, 0.115 mmol). The reaction was purged with nitrogen, then a flow of nitrogen was kept over the reaction. The reaction was stirred for 24 hours and analyzed by HPLC. The mixture was filtered and the solid washed with 5 mL of acetonitrile. The solid was dried in the oven at 40° C. for 18 hours. Yield (3.38 g, 96%).

Example 5

Synthesis of (R)-6-α-Naltrexol Methylbromide from (R) Naltrexone Methylbromide

Triethylamine (1.80 g, 18 mmol, 2.48 mL) and 18.0 mL of dry acetonitrile were added into a round bottom flask. To this mixture was added 98% formic acid (2.29 g, 0.50 mmol, 1.88 mL). The reaction exothermed and was stirred for 20 minutes until the temperature reached room temperature. Naltrexone methylbromide (2.35 g, 5.4 mmol) was added. To this slurry was added Dichloro(p-cymene)ruthenium (II) dimer (24 mg, 0.039 mmol) followed by (1S,2S)-(+)-N-tosyl-diphenylethylene diamine (29 mg, 0.079 mmol). The reaction was purged with nitrogen, then a flow of nitrogen was kept over the reaction. The reaction was stirred for 36 hours and analyzed by HPLC. The mixture was filtered and the solid washed with 5 mL of acetonitrile. The solid was dried in the oven at 40° C. for 18 hours. Yield (2.22 g, 94%).

Example 6

Synthesis of 3-Acetyl-6-α-Oxymorphonol from 3-Acetyl Oxymorphone

Into a round bottom flask was added triethylamine (3.98 g, 39.3 mmol, 5.48 mL) and 25 mL of dry acetonitrile. To this mixture was added 98% formic acid (5.13 g, 111.4 mmol, 4.20 mL). The reaction exothermed and stirred for 30 minutes until the temperature reached room temperature. 3-Acetyloxymorphone (4.50 g, 13.1 mmol) was added. To this slurry was added dichloro(p-cymene)ruthenium (II) dimer (53 mg, 0.0865 mmol) followed by (1S,2S)-(+)-N-tosyl-diphenylethylene diamine (63 mg, 0.173 mmol). The reaction was purged with nitrogen then a flow of nitrogen was kept over the reaction. The reaction was stirred for 48 hours. The mixture was evaporated under vacuum forming a semi solid. The semisolid washed was stirred with 15 mL of acetonitrile. The solid was isolated by filtration, rinsed with acetonitrile (10 mL), and dried in the oven at 40° C. for 18 hours. Yield (4.20 g, 93%, 6-α: 99%).

Example 7

Synthesis of 6-α-Hydromorphol from Hydromorphone

Triethylamine (6.10 g, 60.3 mmol, 8.4 mL) and 25.0 mL of dry acetonitrile were added into a round bottom flask. To this mixture was added 98% formic acid (7.78 g, 0.17 mol, 6.4 mL). The reaction exothermed and was stirred for 30 minutes until the temperature reached room temperature. Hydromorphone base (5.21 g, 18.3 mmol) was added. To this slurry was added Dichloro(p-cymene)ruthenium (II) dimer (50 mg, 0.082 mmol) followed by (1S,2S)-(+)-N-tosyl-diphenylethylene diamine (60 mg, 0.163 mmol). The reaction was purged with nitrogen, then a flow of nitrogen was kept over the reaction. The reaction was stirred for 36 hours and analyzed by HPLC. The mixture was filtered and the solid washed with 5 mL of acetonitrile. The solid was dried in the oven at 40° C. for 18 hours. Yield (4.94 g, 94%).

Example 8

Epimeric Ratios and Yields

Example 8 depicts the conversion of certain 6-keto morphinans (oxymorphone, noroxymorphone, oxycodone, naloxone, and naltrexone) to their corresponding 6-hydroxy morphinans. Specifically, the following table provides the epimeric ratio of 6-α-hydroxy morphinan to 6-β-hydroxy morphinan and the corresponding yields for each compound.

| Name | $R_{17}$ | $R_{311}$ | React. Time (h) | Product | Substrate to Solvent | 6α:6β ratio (area %) | % Yield |
|---|---|---|---|---|---|---|---|
| Oxymorphone | $CH_3$ | H | 24 | Oxymorphol | 1 gm to 5 mL | 99.7:0.3 | 96 |
| Noroxymorphone | H | H | 24 | Noroxymorphol | 1 gm to 5 mL | 99.6:0.4 | 95 |
| Oxycodone | $CH_3$ | $CH_3$ | 8 | Oxycodol | 1 gm to 5 mL | 99.8:0.2 | 94 |
| Naloxone | $CH_2CH=CH_2$ | H | 24 | Naloxol | 1 gm to 7 mL | 99.6:0.4 | 93 |
| Naltrexone | $CH_2$(cyclopropane) | H | 24 | Naltrexol | 1 gm to 7 mL | 99.6:0.4 | 96 |

In addition to the above morphinans, the amine salts of opiates are also viable substrates. For example, the 6-keto group of naltrexone methylbromide was effectively reduced as shown in the table below:

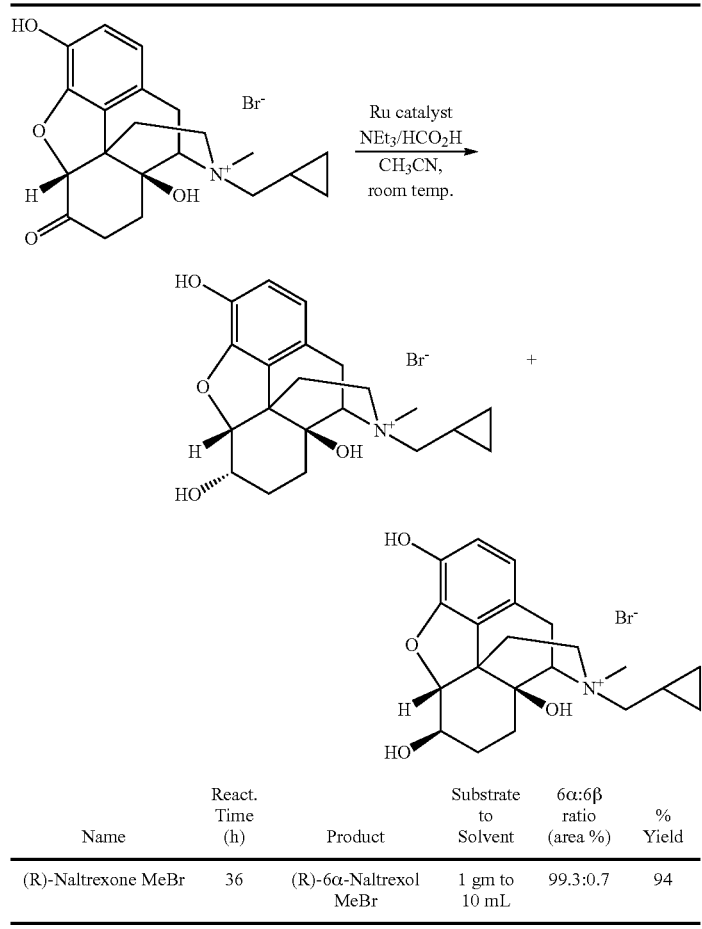

| Name | React. Time (h) | Product | Substrate to Solvent | 6α:6β ratio (area %) | % Yield |
|---|---|---|---|---|---|
| (R)-Naltrexone MeBr | 36 | (R)-6α-Naltrexol MeBr | 1 gm to 10 mL | 99.3:0.7 | 94 |

Hydrocodone and hydromorphone were also subjected to the reduction by hydrogen transfer. The table below indicates the results.

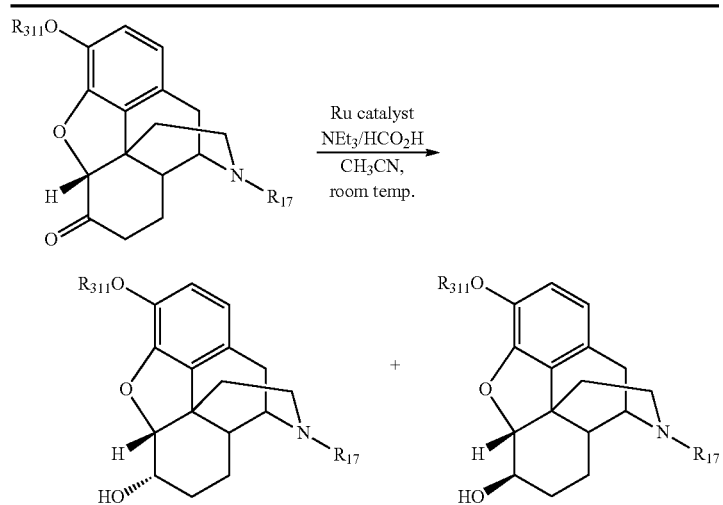

-continued

| Name | $R_{17}$ | $R_{311}$ | React. Time (h) | Product | Substrate to Solvent | 6α:6β ratio (area %) | % Yield |
|---|---|---|---|---|---|---|---|
| Hydrocodone | $CH_3$ | $CH_3$ | 6 | Hydrocodol | 1 gm to 5 mL | 98.2:1.8 | 94 |
| Hydromorphone | $CH_3$ | H | 24 | Hydromorphol | 1 gm to 5 mL | 97.7:2.3 | 96 |

Example 9

Preparation of Nalbuphine

The following reactions depict various methods of synthesizing nalbuphine starting from noroxymorphone. All of the methods comprise the asymmetric catalyst step of converting a 6-keto morphinan to the 6-α-hydroxymorphinan described herein.

Synthesis 9(a)

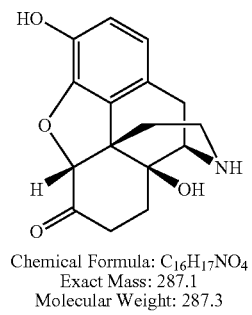

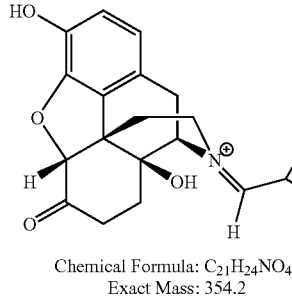

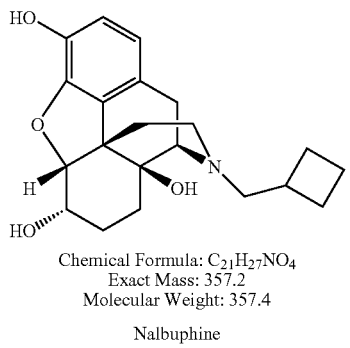

The procedure for this reaction is detailed in Example 3.

Synthesis 9(b)

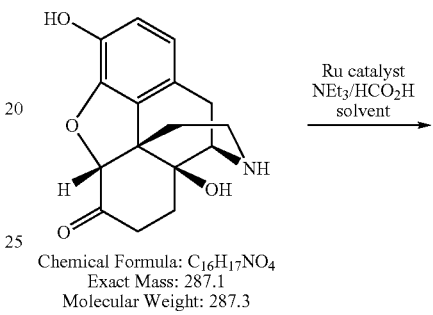

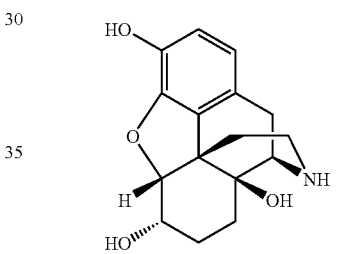

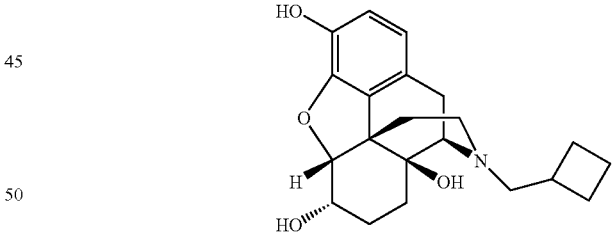

Step 1: Synthesis of 6-α-Noroxymorphol from Noroxymorphone

Into a round bottom flask was added triethylamine (4.57 g, 45.2 mmol, 6.29 mL) and 20 mL of dry acetonitrile. To this mixture was added 98% formic acid (5.82 g, 126.4 mmol, 4.77 mL). The reaction exothermed and was stirred for 30 minutes until the temperature reached room temperature. Noroxxymorphone (3.93 g, 13.7 mmol) was added. To this slurry was added dichloro(p-cymene)ruthenium (II) dimer (39 mg, 0.0637 mmol) followed by (1S,2S)-(+)-N-tosyldiphenylethylene diamine (47 mg, 0.128 mmol). The reaction was purged with nitrogen, then a flow of nitrogen was kept over the reaction. The reaction was stirred for 48 hours and analyzed by HPLC (6-α-noroxymorphol 99.6%, 6-β-noroxymorphol 0.4%). The mixture was evaporated to a solid. The solid was stirred with 15 mL of acetonitrile. The product (as the formate salt) was then isolated by filtration, washing the solid with acetonitrile (10 mL). The formate salt was slurried in acetonitrile (10 mL) then 29% $NH_3/H_2O$ was added dropwise to pH 10.0. A precipitate formed, which was filtered, and then rinsed with acetonitrile (10 mL). The solid was dried in the oven at 40° C. for 18 hours. Yield (3.76 g, 95%).

Step 2: Synthesis of Nalbuphine from 6-α-Noroxymorphol

6-α-Noroxymorphol hydroformate salt (4.10 g, 12.2 mmole) was dissolved in anhydrous methanol (20 mL). To this solution was added cyclobutanecarboxaldehyde (2.05 g, 24.4 mmol). A white precipitate formed and was stirred at room temperature for 3 hours. $NaBH_4$ (470 mg, 12.2 mmol) was then added in four portions and stirred at room temperature for 16 hours. HPLC analysis indicated the reaction was complete. Acetone (5 mL) was added and stirred for 30 minutes. The entire reaction mixture was evaporated then slurried in distilled water (5 mL). The pH was adjusted to 9.0 using 29% $NH_3$. After stirring for 30 minutes, nalbuphine (3.5 g, 80% yield) was isolated by filtration, washing the solid with acetonitrile (10 mL), and drying at 50° C. for 48 hours.

Step 2: Synthesis of 3, N-DCBC-6-α-Noroxymorphol from 6-α-Noroxymorphol

6-α-Noroxymorphol (2.63 g, 9.1 mmol) was dissolved in anhydrous THF (50 mL). Triethylamine (1.93 g, 19.1 mmol, 2.66 mL) was added. The reaction was cooled to 5° C. (ice/water bath) then cyclobutanecarbonyl chloride (2.16 g, 18.2 mmol, 2.07 mL) was added dropwise. After the addition was complete, the reaction was warmed to room temperature and stirred for 18 hours. Triethylamine hydrochloride was removed by filtration rinsing the solid with anhydrous THF (15 mL) and the filtrate was evaporated to a thick oil. This oil was dissolved in ethyl acetate (25 mL) and washed with 1.0 M HCl (2×25 mL) and distilled water (25 mL). After drying over anhydrous $MgSO_4$, filtering, evaporation of the solvent, and drying under high vacuum for 16 hours at room temperature, 3, N-dicyclobutylcarbonyl-6-α-noroxymorphol (4.10 g, 99% yield) was obtained.

Step 3: Synthesis of Nalbuphine from 3, N-DCBC-6-α-Noroxymorphol

Into a dried flask under nitrogen was introduced THF (100 mL). To this solvent, $LiAlH_4$ (1.34 g, 35.3 mmol) was added carefully in 4 portions. To the $LiAlH_4$ solution was added dropwise a solution of 3, N-DCBC-6-α-noroxymorphol (4.0 g, 8.8 mmol) in 100 mL anhydrous THF. The reaction stirred at room temperature for 2 hours. HPLC analysis indicated that the reaction was complete. Ethyl acetate (5.0 mL) was

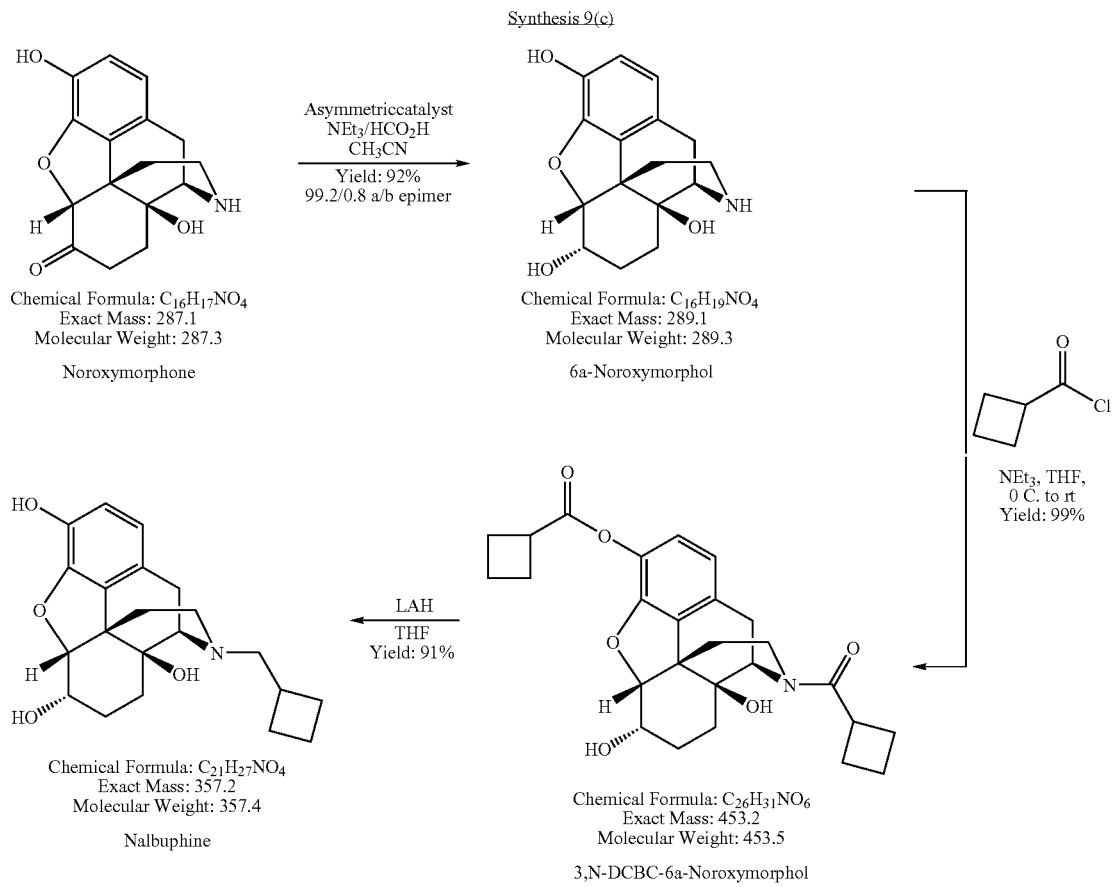

Synthesis 9(c)

Step 1: Synthesis of 6-α-Noroxymorphol from Noroxymorphone

The synthesis of 6-α-noroxymorphol from noroxymorphone is as previously described in Synthesis 9(b).

added dropwise then stirred for 1 hour. Then, 5% HCl (100 mL) was added dropwise and stirred for an additional hour. 29% aqueous ammonia was added until the pH~9.2. The mixture was filtered producing a tan solid. The filtrate was extracted with ethyl acetate (3×100 mL), dried over anhydrous MgSO₄, filtered, and evaporated to a semi solid. The tan solid and semi solid were slurried at room temperature with acetonitrile (5 mL) for 4 hours, filtered, and washed with acetonitrile (5 mL). The obtained nalbuphine (2.88 g, 91% yield, 6-α: 99%) was isolated as an off-white solid.

added >96% HCO₂H (9.25 g, 201.0 mmol, 7.6 mL) dropwise. After the addition was complete, an additional 10 mL of acetonitrile was added. This salt mixture was degassed with nitrogen gas for 15 minutes. Then, a solution of 3,N-DCBC-noroxymorphone in acetonitrile (10 mL) was added. To this solution was added dichloro(p-cymene)ruthenium (II) dimer

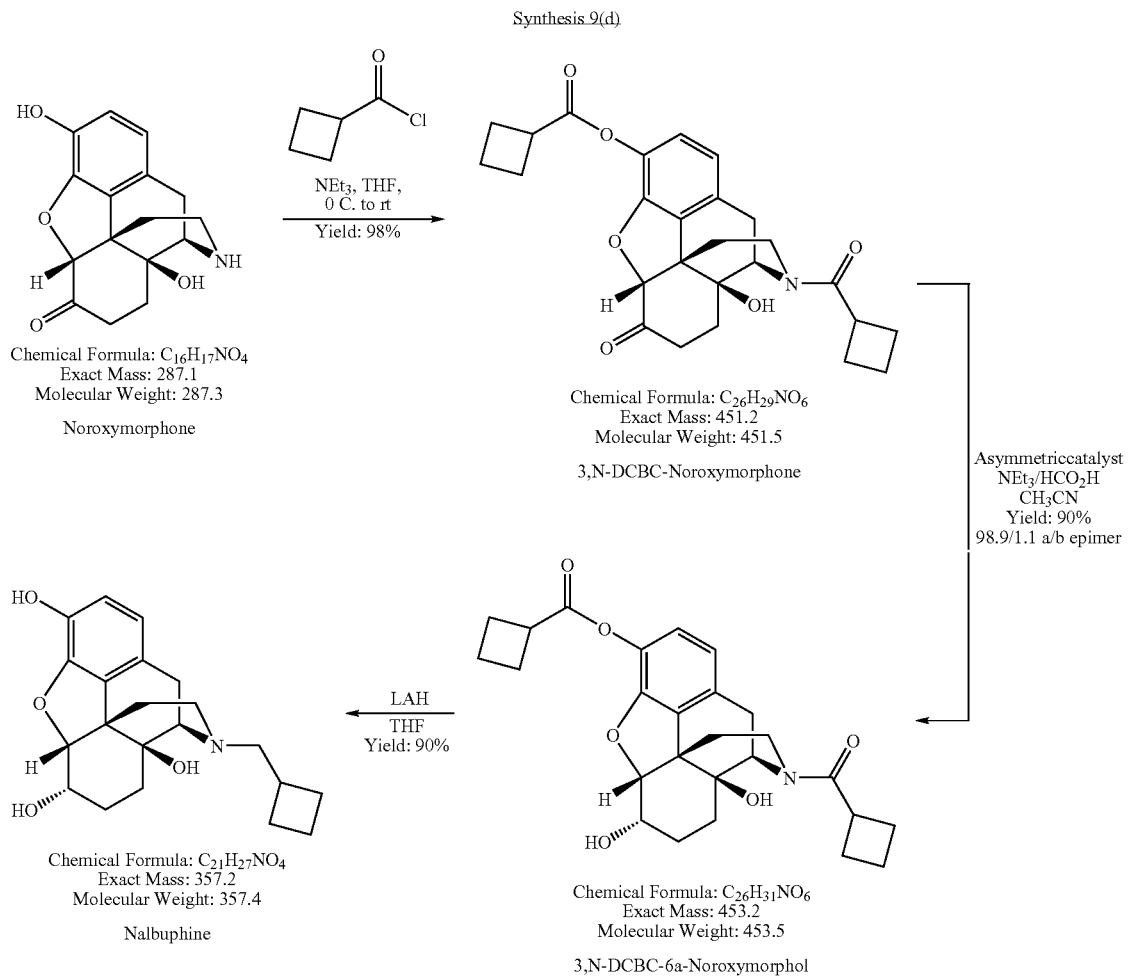

Synthesis 9(d)

Step 1: Synthesis of 3, N-DCBC-Noroxymorphone from Noroxymophone

Into a dried flask was added noroxymorphone (7.70 g, 26.8 mmol), tetrahydrofuran (anhydrous, 35 mL), then triethylamine (5.70 g, 56.3 mmol, 7.9 mL). The mixture was cooled to 5° C. (ice/H₂O) then cyclobutanecarbonyl chloride (6.36 g, 53.6 mmol, 6.11 mL) was added dropwise. After the addition was complete, the reaction was warmed to room temperature and stirred for 16 hours. HPLC analysis indicated the reaction was complete. The reaction was filtered rinsing the solid with 10 mL of tetrahydrofuran. The filtrate was evaporated under reduced pressure producing a thick oil. The oil was dissolved in CHCl₃ (100 mL). The chloroform solution was then washed with 5% HCl/H₂O (2×25 mL), dried over anhydrous MgSO₄ (5 g), filtered and evaporated to dryness producing the product (12.05 g, 99% yield).

Step 2: Synthesis of 6-α-3, N-DCBC-Noroxymorphol from 3, N-DCBC-Noroxymorphone

Into a dried flask was added acetonitrile (10 mL) and triethylamine (8.14 g, 80.4 mmol, 11.2 mL). To this mixture was (40 mg, 0.0653 mmol) followed by (1S,2S)-(+)-N-tosyl-diphenylethylene diamine (33 mg, 0.090 mmol). The reaction was degassed then stirred at room temperature for 72 hours. At that time, dichloro(p-cymene)ruthenium (II) dimer (39 mg, 0.0637 mmol) followed by (1S,2S)-(+)-N-tosyl-diphenylethylene diamine (47 mg, 0.128 mmol) was added. The reaction was stirred for 10 days at room temperature having a slow purge of nitrogen. HPLC analysis indicated that the reaction was complete. Evaporation of the reaction mixture under reduced pressure produced a thick oil (12.1 g, 99% yield), which used directly to form nalbuphine.

Step 3: Synthesis of Nalbuphine from 6-α-3, N-DCBC-Noroxymorphol

Into a dried flask under nitrogen was introduced THF (60 mL). To this solvent, LiAlH₄ (1.76 g, 46.4 mmol) was added carefully in 4 portions. To the LiAlH₄ solution was added dropwise a solution of 3, N-DCBC-6-α-noroxymorphol (6.15 g, 13.6 mmol) in 40 mL anhydrous THF. The reaction stirred at room temperature for 1 hour then warmed to reflux for 3 hours. HPLC analysis indicated the reaction was complete. The reaction was cooled to 5° C. (ice/water) then ethyl acetate (5.0 mL) was added dropwise then stirred for 1 hour. Finally, 5% HCl (100 mL) was added dropwise and stirred for an additional hour. 29% aqueous ammonia was added until the pH~9.2. The mixture was filtered producing a tan solid. The filtrate extracted with ethyl acetate (3×100 mL), dried over anhydrous MgSO$_4$, filtered, and evaporated to a semi solid. The tan solid and semi solid were slurried at room temperature with acetonitrile (10 mL) for 4 hours, filtered, and washed with acetonitrile (5 mL). The obtained nalbuphine (4.86 g, 90% yield, 6-α: 99%) was isolated as an off-white solid.

were stirred at room temperature for 20 days. HPLC analysis indicated that the reaction was complete. Distilled water (100 mL) was added and the mixture was stirred at room temperature. The mixture was evaporated under vacuum to a thick oil. Distilled water (15 mL) was added and the pH was adjusted to 9.0 using 29% NH$_3$/H$_2$O. A solid formed which was filtered then rinsed with distilled water (10 mL). The solid was stirred for 6 hours in acetonitrile (25 mL), filtered, washed with acetonitrile (10 mL), and dried at 50° C. for 48 hours yielding nalbuphine (1.64 g, 60% yield, 6-α: 99%) as an off-white solid.

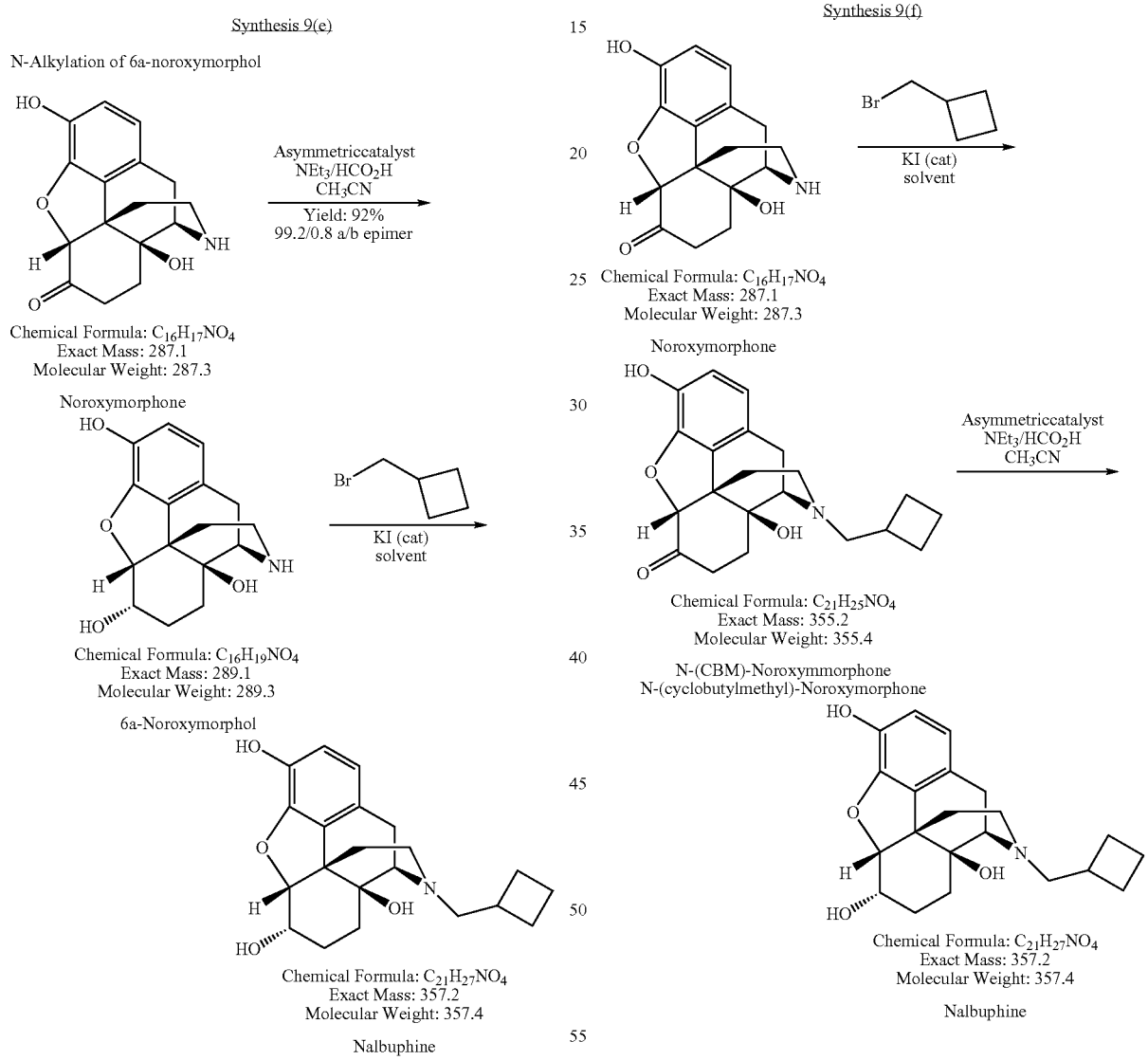

Step 1: Synthesis of 6-α-Noroxymorphol from Noroxymorphone

The synthesis of 6-α-noroxymorphol from noroxymorphone is as previously described in Synthesis 9(b).

Step 2: Synthesis of Nalbuphine from 6-α-Noroxymorphol

Into a dried flask was added 6-α-noroxymorphol (2.22 g, 7.7 mmol) and dimethylacetamide (DMAc) (20 mL). To this solution was added potassium bicarbonate (850 mg, 8.5 mmol), cyclobutanemethyl bromide (1.14 g, 7.6 mmol, 0.86 mL), and potassium iodide (1.26 g, 7.7 mmol). The contents Step 1: Synthesis of N-(cyclobutylmethyl)-Noroxymorphone from Noroxymorphone Noroxymorphone (1.59 g, 5.5 mmol), potassium carbonate (0.61 g, 6.1 mmol), potassium iodide (0.46 g, 2.8 mmol), and dimethyl acetamide (10 mL) were added into a round bottom flask. Bromomethylcyclobutane (0.82 g, 5.5 mmol, 0.62 mL) was added. The reaction was stirred for 7 days at room temperature. At that time, bromomethylcyclobutane (0.82 g, 5.5 mmol, 0.62 mL) was added. The reaction was stirred for an additional 7 days. HPLC analysis indicated that the noroxymorphone was consumed. Distilled water (50 mL) was added and stirred at room temperature for 6 hours. An off-white precipitate formed, which was removed by filtration. The solid was washed with distilled water (25 mL), then slurried for 24 hours in acetonitrile (25 mL). Filtration, washing the solid with acetonitrile (10 mL), and drying at room temperature under vacuum for 24 hours yielded N-(cyclobutylmethyl)-noroxymorphone (1.43 g, 73% yield) as a tan solid.

Step 2: Synthesis of Nalbuphine from N-(cyclobutylmethyl)-Noroxymorphone

Into a dried flask was added triethylamine (0.87 g, 8.6 mmol, 1.2 mL) and acetonitrile (5 mL). To this solution was added >96% HCO$_2$H (0.99 g, 21.5 mmol, 0.81 mL). After stirring under nitrogen for 15 minutes, N-(cyclobutylmethyl)-noroxymorphone (1.02 g, 2.9 mmol) was added. Then, dichloro(p-cymene)ruthenium (II) dimer (10 mg, 0.0163 mmol) followed by (1S, 2S)-(+)-N-tosyl-diphenylethylene diamine (12 mg, 0.033 mmol) were added. This reaction was stirred for 72 hours at room temperature. HPLC analysis indicated that the reaction was complete. The reaction mixture was evaporated under reduced pressure forming a thick brown oil. Slurring the oil in acetonitrile (15 mL) for 18 hours yielded a brown solid. The solid was isolated by filtration, which was washed with acetonitrile (10 mL), Drying the solid yielded nalbuphine (0.85 g, 83% yield, 6-α: 99%) as a tan solid.

Example 10

Preparation of (+)Hydrocodol (+)-Hydrocodol was prepared from (+)-hydrocodon according to the following reaction scheme:

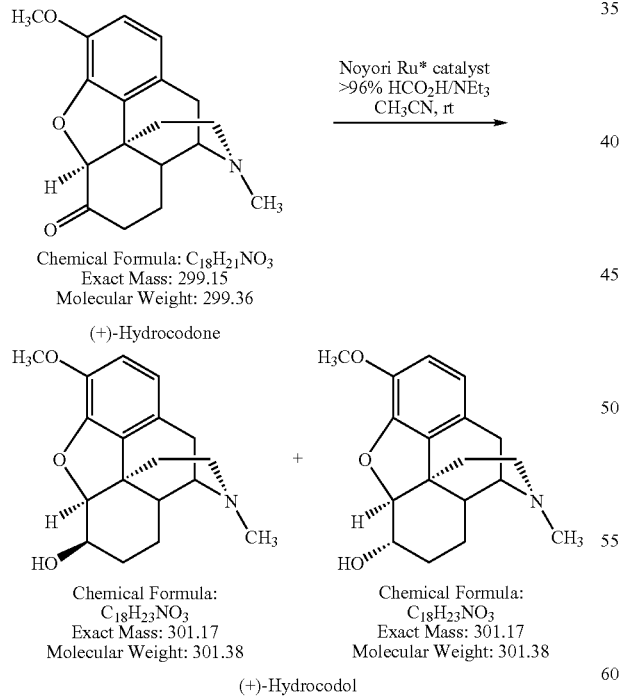

(+)-Hydrocodone (0.31 g, 1.03 mmol) and acetonitrile (CH$_3$CN; 1 mL) were added to a dried flask. Triethylamine (NEt$_3$; 0.63 g, 6.21 mmol, 0.87 mL) and acetonitrile (1 mL) were added to this solution, and >96% formic acid (CHO$_2$H; 0.38 g, 8.24 mmol, 0.31 mL) was added dropwise into the solution. The solution was stirred for 15 minutes at room temperature. Then, Dichloro(p-cymene)Ru(II) dimer (3 mg, 0.005 mmol) and (1S,2S)-(+)-p-tosyl-1,2-diphenylethylenediamine (3 mg, 0.009 mmol) were added, and the walls of the flask were rinsed with an additional amount of acetonitrile (3 mL) to ensure the catalysts were introduced into the mixture. The reaction was stirred at room temperature for 72 hr. HPLC analysis indicated that the reaction went to completion. The reaction solution was evaporated to an oily solid. This oily solid was dissolved with 29% NH$_3$/H$_2$O (5 mL), then extracted with chloroform (3×10 mL). The extracts were combined and evaporated to dryness. (+)-Hydrocodol (0.21 g, 70% yield, 6-α: 99.3%) was isolated by column chromatography (silica gel 60, 5.0 g) using 25% iso-propanolichloroform as the eluent and the desired fractions were evaporated to dryness.

Example 11

Preparation of (+)-α-Naltrexol (+)-α-Naltrexol was prepared from (+)-naltrexone according to the following reaction scheme:

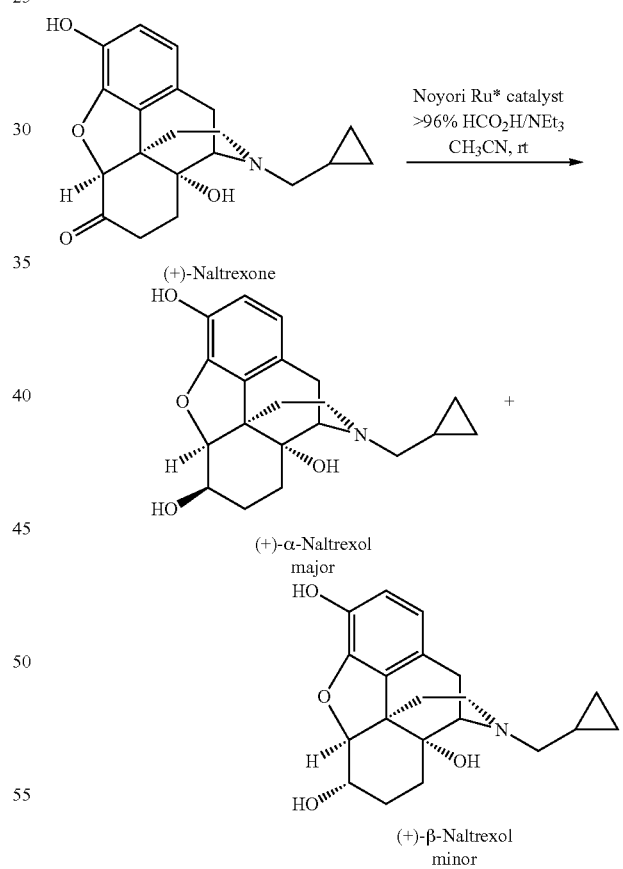

(+)-Naltrexone (250 mg) was dissolved in a solution of HCO$_2$H/Et$_3$N (mol ratio 5:3, 1 mL) in acetonitrile (3 mL). The solution was purged with nitrogen with stiffing and then kept under a nitrogen atmosphere. 10 Mg of Dichloro(p-cymene)Ru(II) dimer with the (1S,2S)-(+)-p-tosyl-1,2-diphenylethylenediamine ligand were added. The reaction was stirred at room temperature for 20 hr. HPLC analysis indicated that the reaction was complete. Water (15 mL) was added. The aqueous acetonitrile phase was extracted with chloroform (2×15 mL) to remove the catalyst. The pH of the aqueous solution was adjusted to 10 using c-NH$_4$OH followed by extraction with chloroform (2×15 mL). The combined chloroform layers were washed with water (2×5 mL). The volatile solvents were removed under reduced pressure with mild heating. 180 Mgs of solid that was substantially made-up of (+)-α-Naltrexol was isolated.

Example 12

Preparation of (+)-α-Naloxol (+)-α-Naloxol was prepared from (+)-naloxone according to the following reaction scheme:

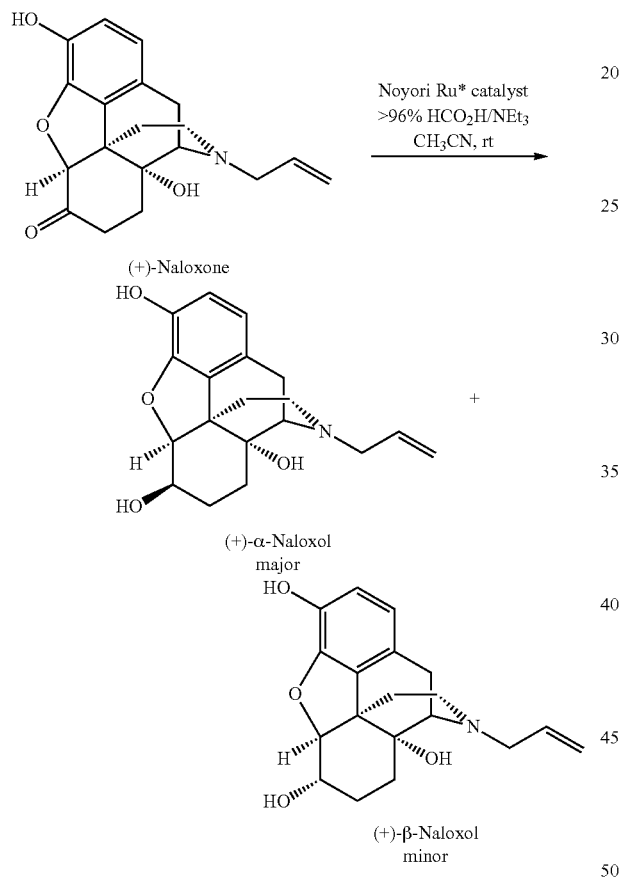

(+)-Naloxol (250 mg) was dissolved in a solution of HCO$_2$H/ Et$_3$N (mol ratio 5:3, 1 mL) in acetonitrile (3 mL). The solution was purged with nitrogen with stirring and then kept under a nitrogen atmosphere. 10 Mg of Dichloro(p-cymene)Ru(II) dimer with the (1S,2S)-(+)-p-tosyl-1,2-diphenylethylenediamine ligand were added. The reaction was stirred at room temperature for 20 hr. HPLC analysis indicated that the reaction was complete. Water (15 mL) was added. The aqueous acetonitrile phase was extracted with chloroform (2×15 mL) to remove the catalyst. The pH of the aqueous solution was adjusted to 10 using c-NH$_4$OH followed by extraction with chloroform (2×15 mL). The combined chloroform layers were washed with water (2×5 mL). The volatile solvents were removed under reduced pressure with mild heating. 170 Mgs of solid that contained (+)-α-Naloxol in a mixture was isolated.

What is claimed is:
1. A process for the preparation of a 6-hydroxy morphinan (II) having the formula

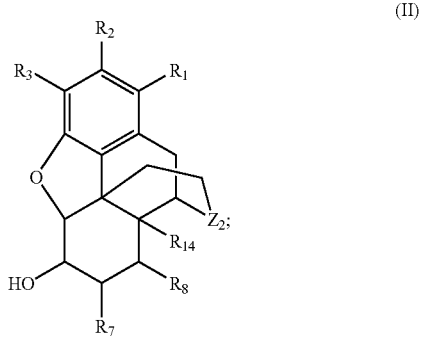

the process comprising reducing a 6-keto morphinan (I) in the presence of a ruthenium, rhodium, or iridium asymmetric catalyst and a hydrogen source, the 6-keto morphinan (I) having the formula:

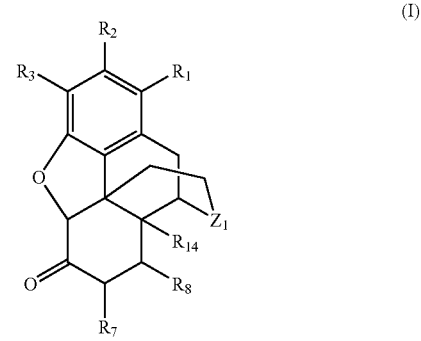

wherein
$R_1$ is hydrogen, hydrocarbyl, substituted hydrocarbyl, halo, or —OR$_{111}$;
$R_2$ is hydrogen, hydrocarbyl, substituted hydrocarbyl, halo, or —OR$_{211}$;
$R_3$ is hydrogen, hydrocarbyl, substituted hydrocarbyl, or —OR$_{311}$;
$R_7$ is hydrogen, hydrocarbyl, substituted hydrocarbyl, or —OR$_{711}$;
$R_8$ is hydrogen, hydrocarbyl, substituted hydrocarbyl, or —OR$_{811}$;
$R_{14}$ is hydrogen or hydroxy;
$R_{111}$ is hydrogen, hydrocarbyl, substituted hydrocarbyl, or a hydroxy protecting group;
$R_{211}$ is hydrogen, hydrocarbyl, substituted hydrocarbyl, or a hydroxy protecting group;
$R_{311}$ is hydrogen, hydrocarbyl, substituted hydrocarbyl, or a hydroxy protecting group;
$R_{711}$ is hydrogen, hydrocarbyl, substituted hydrocarbyl, or a hydroxy protecting group;
$R_{811}$ is hydrogen, hydrocarbyl, substituted hydrocarbyl, or a hydroxy protecting group;
$Z_1$ is >N(R$_9$), >N$^+$(R$_9$)(R$_{10}$), >NCH(OH)(R$_9$), or >N$^+$=CH(R$_9$);

$Z_2$ is
(i) $Z_1$ when $Z_1$ is >N($R_9$) or >$N^+$($R_9$)($R_{10}$); or
(ii) >$NCH_2$($R_9$) when $Z_1$ is >NCH(OH)$R_9$ or >$N^+$=CH($R_9$); and $R_9$ and $R_{10}$ are independently hydrogen, acyl, hydrocarbyl, substituted hydrocarbyl, or heterocyclo.

2. The process of claim 1, wherein the 6-hydroxy morphinan (II) product is a mixture of 6-alpha-hydroxy and 6-beta-hydroxy morphinan epimers.

3. The process of claim 2, wherein the epimeric ratio of 6-alpha-hydroxy to 6-beta-hydroxy morphinan epimers is chosen from greater than 9:1, greater than 19:1, and greater than 99:1.

4. The process of claim 1, wherein the catalyst comprises a ruthenium complex or a rhodium complex.

5. The process of claim 1, wherein the catalyst is chosen from:
dichloro(arene)Ru(II) dimer, dichloro(pentamethylcyclopentadienyl)Rh(II) dimer, BINAP-Ru (II) diacetate, BINAP-Ru (II) dichloride, BINAP-Ru (II) dibromide, BI NAP-Ru (II) diiodide, [RuCl((R or S)BINAP)($C_6H_6$)]Cl, or dichloro(pentamethylcyclopentadienyl) iridium (III) dimer;
bidentate, chiral ligand complexed with the ruthenium, rhodium, or iridium complex via nitrogen, oxygen, or phosphorous donor atoms; and
a chiral ligand having the Formula (670), Formula (680), Formula (690), or Formula (700):

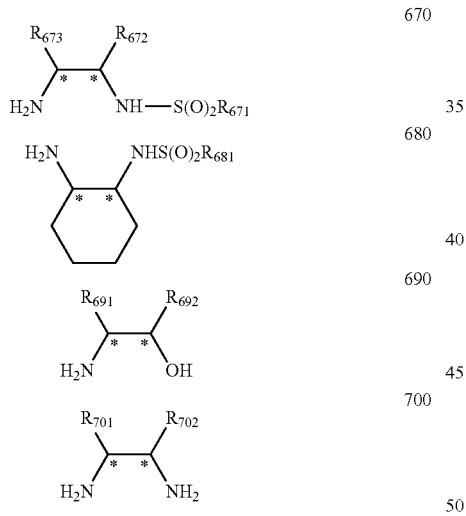

wherein
$R_{671}$, $R_{672}$, $R_{673}$, $R_{681}$, $R_{691}$, $R_{692}$, $R_{701}$, and $R_{702}$ are independently alkyl or aryl and wherein $R_{691}$ and $R_{692}$, and the carbon atoms to which they are attached, may optionally form a cyclic or bicyclic compound.

6. The process of claim 5, wherein the ligand is chosen from:
the Formula (670) and $R_{672}$ and $R_{673}$ are phenyl; $R_{671}$ is aryl; and $R_{671}$ is tolyl, mesityl, or naphthyl;
the Formula (680) and $R_{681}$ is tolyl, mesityl, 2,4,6-triisopropylphenyl, or naphthyl; and
the Formula (700) and $R_{701}$ and $R_{702}$ are hydrogen.

7. The process of claim 5, wherein the ligand is (1S,2S)-(+)-N-4-toluenesulfonyl-1,2-diphenylethylene-1,2-diamine, (1R,2R)-(−)-N-4-toluenesulfonyl-1,2-diphenylethylene-1,2-diamine, dl-N-tosyl-1,2-diphenylethylenediamine, N-tosyl-1,2-diphenylethylenediamine, N-tosyl-1,2-ethylenediamine, or N-tosyl-1,2-diaminocyclohexane.

8. The process of claim 1, wherein the catalyst is selected from the group consisting of

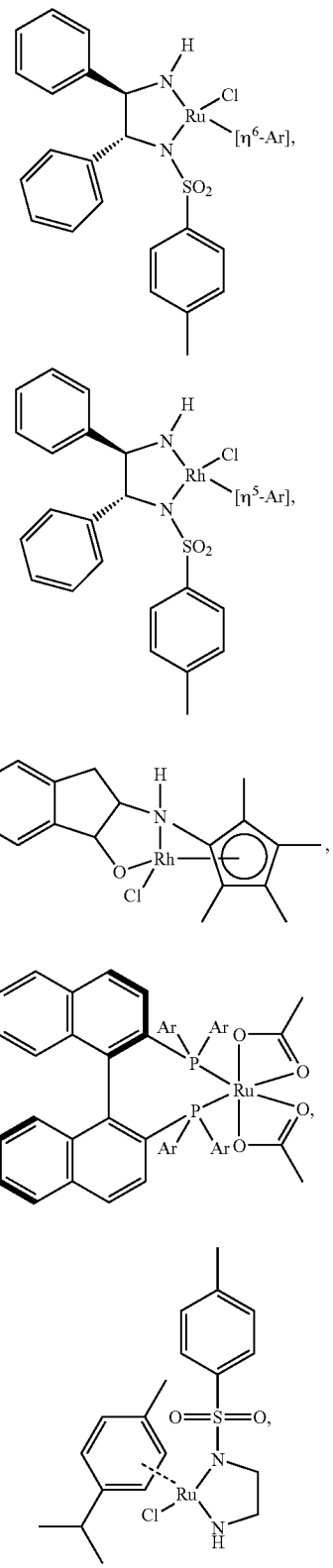

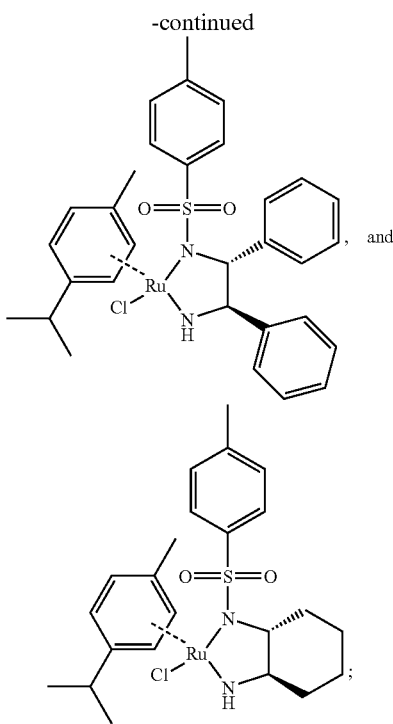

wherein
Ar is aryl.

9. The process of claim 1, wherein the catalyst is a Noyori catalyst.

10. The process of claim 1, wherein the hydrogen source comprises protic compounds; the process occurs in an aprotic, polar solvent; and the process occurs within a temperature range of about 20° C. to about 40° C.

11. The process of claim 10, wherein the hydrogen source is a mixture of formic acid and triethylamine; and the ratio of formic acid to triethylamine is about 5:2.

12. The process of claim 1, wherein $R_1$ is hydrogen or —$OR_{111}$ and $R_{111}$ is hydrogen, alkyl, acyl, alkaryl, aryl, or a hydroxy protecting group; $R_2$ is hydrogen or —$OR_{211}$ and $R_{211}$ is hydrogen, alkyl, acyl, alkaryl, aryl, or a hydroxy protecting group; $R_3$ is hydrogen or —$OR_{311}$ and $R_{311}$ is hydrogen, alkyl, acyl, alkaryl, aryl, or a hydroxy protecting group; and $R_{311}$ is hydrogen or alkyl.

13. The process of claim 1,
wherein
$R_1$ is hydrogen;
$R_2$ is hydrogen;
$R_3$ is —$OR_{311}$; and
$R_{311}$ is hydrogen or $C_{1-8}$alkyl.

14. The process of claim 13, wherein $R_7$ is hydrogen, $C_{1-8}$ alkyl, or $C_{1-8}$ substituted alkyl; $R_8$ is hydrogen; $R_{14}$ is hydroxyl; $Z_1$ and $Z_2$ are >N($R_9$) and $R_9$ is hydrogen, or substituted or unsubstituted $C_{1-8}$ alkyl, $C_{2-8}$ alkenyl, aryl or heterocyclo.

15. The process of claim 1,
wherein
$Z_1$ and $Z_2$ are >N$^+$($R_9$)($R_{10}$); and
$R_9$ and $R_{10}$ are independently hydrogen, acyl, or substituted or unsubstituted $C_{1-8}$ alkyl, $C_{2-8}$ alkenyl, aryl or heterocyclo.

16. The process of claim 15 wherein $R_9$ and $R_{10}$ are independently hydrogen, methyl, ethyl, propyl, cyclopropyl, cyclopropylmethyl, butyl, isobutyl, t-butyl, cyclobutyl, cyclobutylmethyl, or allyl.

17. The process of claim 15, wherein $R_9$ is cyclopropylmethyl and $R_{10}$ is methyl.

18. The process of claim 1,
wherein
$Z_1$ is >NCH(OH)($R_9$);
$Z_2$ is >NCH$_2$($R_9$); and
$R_9$ is hydrogen, acyl, or substituted or unsubstituted $C_{1-8}$ alkyl, $C_{2-8}$ alkenyl, aryl or heterocyclo.

19. The process of claim 1,
wherein
$Z_1$ is >N$^+$=CH($R_9$);
$Z_2$ is >NCH$_2$($R_9$); and
$R_9$ is hydrogen, acyl, or substituted or unsubstituted $C_{1-8}$ alkyl, $C_{2-8}$ alkenyl, aryl or heterocyclo.

20. The process of claim 1,
wherein
$R_1$ is hydrogen;
$R_2$ is hydrogen;
$R_3$ is —$OR_{311}$;
$R_7$ is hydrogen;
$R_8$ is hydrogen;
$R_{14}$ is hydroxy;
$R_{311}$ is hydrogen;
$Z_1$ is >N($R_9$); and
$R_9$ is cyclobutylmethyl.

21. The process of claim 1,
wherein
$R_1$ is hydrogen;
$R_2$ is hydrogen;
$R_3$ is —$OR_{311}$;
$R_7$ is hydrogen;
$R_8$ is hydrogen;
$R_{14}$ is hydroxy;
$R_{311}$ is hydrogen;
$Z_1$ is >N$^+$=CH($R_9$);
$Z_2$ is >NCH$_2$($R_9$); and
$R_9$ is cyclobutyl.

* * * * *